(12) United States Patent
Gustafson et al.

(10) Patent No.: US 12,226,092 B2
(45) Date of Patent: Feb. 18, 2025

(54) KNOTLESS SUTURE ANCHORING USING TWO AWL SHAFTS

(71) Applicant: Medos International Sarl, Le Locle (CH)

(72) Inventors: Adam Gustafson, Dighton, MA (US); Stefan Gabriel, Mattapoisett, MA (US)

(73) Assignee: Medos International Sarl, Le Locle (CH)

( * ) Notice: Subject to any disclaimer, the term of this patent is extended or adjusted under 35 U.S.C. 154(b) by 318 days.

(21) Appl. No.: 17/963,400

(22) Filed: Oct. 11, 2022

(65) Prior Publication Data

US 2023/0118876 A1 Apr. 20, 2023

Related U.S. Application Data

(60) Continuation of application No. 16/709,634, filed on Dec. 10, 2019, now Pat. No. 11,497,483, which is a
(Continued)

(51) Int. Cl.
| | |
|---|---|
| *A61B 17/04* | (2006.01) |
| *A61B 17/16* | (2006.01) |
| *A61B 17/88* | (2006.01) |

(52) U.S. Cl.
CPC ...... *A61B 17/0401* (2013.01); *A61B 17/1604* (2013.01); *A61B 2017/0409* (2013.01);
(Continued)

(58) Field of Classification Search
CPC ............ A61B 17/0401; A61B 17/1604; A61B 17/8888; A61B 2017/0409;
(Continued)

(56) References Cited

U.S. PATENT DOCUMENTS

| | | |
|---|---|---|
| 5,690,676 A | 11/1997 | DiPoto et al. |
| 5,741,282 A | 4/1998 | Anspach, III et al. |

(Continued)

FOREIGN PATENT DOCUMENTS

| | | |
|---|---|---|
| JP | 2016105840 A | 6/2016 |
| WO | WO-2011059995 A2 | 5/2011 |

(Continued)

OTHER PUBLICATIONS

European Search Report for EP App. No. 18185841.6 dated Dec. 17, 2018 (7 pages).

*Primary Examiner* — Phong Son H Dang
(74) *Attorney, Agent, or Firm* — Mintz Levin Cohn Ferris Glovsky and Popeo, P.C.

(57) ABSTRACT

Methods and systems are provided for securing tissue to bone. A surgical system can include a driver having a proximal handle and a driver shaft extending therefrom, a distal awl shaft, a proximal awl shaft separate from the distal awl shaft and movable with respect to the distal awl shaft, a suture anchor, and a dilator feature distal to the suture anchor. The distal and proximal awl shafts are receivable in at least part of a lumen of the driver. In a bone forming configuration of the system, in which the distal awl shaft is driven into bone, a distal end of the proximal awl shaft abuts a proximal end of the distal awl shaft. The proximal awl shaft can be moved proximally, such as by activating an awl handle coupled thereto, with respect to the distal awl shaft to move the system in a suture anchor insertion configuration.

11 Claims, 20 Drawing Sheets

Related U.S. Application Data division of application No. 15/661,901, filed on Jul. 27, 2017, now Pat. No. 10,639,026.

(52) U.S. Cl.
CPC . *A61B 2017/044* (2013.01); *A61B 2017/0445* (2013.01); *A61B 2017/0448* (2013.01); *A61B 2017/0456* (2013.01); *A61B 17/8888* (2013.01)

(58) Field of Classification Search
CPC ...... A61B 2017/044; A61B 2017/0448; A61B 2017/0456
See application file for complete search history.

(56) References Cited

U.S. PATENT DOCUMENTS

| | | |
|---|---|---|
| 6,319,252 B1 | 11/2001 | McDevitt et al. |
| 6,527,794 B1 | 3/2003 | McDevitt et al. |
| 6,544,281 B2 | 4/2003 | ElAttrache et al. |
| 6,641,597 B2 | 11/2003 | Burkhart et al. |
| 6,673,094 B1 | 1/2004 | McDevitt et al. |
| 6,733,506 B1 | 5/2004 | McDevitt et al. |
| 6,770,073 B2 | 8/2004 | McDevitt et al. |
| 7,329,272 B2 | 2/2008 | Burkhart et al. |
| 7,867,264 B2 | 1/2011 | McDevitt et al. |
| 7,896,907 B2 | 3/2011 | McDevitt et al. |
| 7,993,369 B2 | 8/2011 | Dreyfuss |
| 8,012,174 B2 | 9/2011 | ElAttrache et al. |
| 8,372,124 B2 | 2/2013 | Paulk et al. |
| 8,430,909 B2 | 4/2013 | Dreyfuss |
| 8,613,756 B2 | 12/2013 | Lizardi et al. |
| 8,663,279 B2 | 3/2014 | Burkhart et al. |
| 8,771,315 B2 | 7/2014 | Lunn et al. |
| 8,834,543 B2 | 9/2014 | McDevitt et al. |
| 8,951,292 B2 | 2/2015 | Paulk et al. |
| 9,005,246 B2 | 4/2015 | Burkhart et al. |
| 9,113,859 B2 | 8/2015 | Dooney, Jr. et al. |
| 9,138,220 B2 | 9/2015 | Hernandez |
| 9,179,907 B2 | 11/2015 | ElAttrache et al. |
| 9,226,817 B2 | 1/2016 | Dougherty et al. |
| 9,277,910 B2 | 3/2016 | Nason et al. |
| 9,295,460 B2 | 3/2016 | Hoof et al. |
| 9,314,240 B2 | 4/2016 | Paulk et al. |
| 9,386,977 B2 | 7/2016 | Lunn et al. |
| 9,393,006 B2 | 7/2016 | Housman et al. |
| 9,526,488 B2 | 12/2016 | Arai et al. |
| 9,526,492 B2 | 12/2016 | Lombardo et al. |
| 9,526,494 B1 | 12/2016 | Lanois et al. |
| 9,566,060 B2 | 2/2017 | Dougherty et al. |
| 10,639,026 B2 | 5/2020 | Gustafson et al. |
| 10,751,161 B2 | 8/2020 | Diduch et al. |
| 11,382,613 B1* | 7/2022 | Zenz-Olson ....... A61B 17/0401 |
| 11,497,483 B2 | 11/2022 | Gustafson et al. |
| 2008/0208253 A1 | 8/2008 | Dreyfuss et al. |
| 2009/0281581 A1 | 11/2009 | Berg |
| 2010/0016893 A1 | 1/2010 | Fanton |
| 2011/0118762 A1 | 5/2011 | Dooney, Jr. et al. |
| 2012/0022588 A1 | 1/2012 | Berg |
| 2012/0150225 A1 | 6/2012 | Burkhart et al. |
| 2013/0123845 A1 | 5/2013 | Paulk et al. |
| 2013/0150885 A1 | 6/2013 | Dreyfuss |
| 2013/0165963 A1 | 6/2013 | Coleman et al. |
| 2013/0267998 A1 | 10/2013 | Vijay et al. |
| 2014/0222072 A1 | 8/2014 | Gerber et al. |
| 2014/0257381 A1 | 9/2014 | Palese |
| 2014/0364906 A1 | 12/2014 | Palese et al. |
| 2015/0012015 A1 | 1/2015 | Berelsman et al. |
| 2015/0119937 A1 | 4/2015 | Lunn et al. |
| 2015/0182233 A1 | 7/2015 | Van Wyk et al. |
| 2015/0196290 A1 | 7/2015 | Lanois et al. |
| 2015/0245901 A1* | 9/2015 | Dougherty ............ A61F 2/0805 |
| | | 606/232 |
| 2015/0265270 A1 | 9/2015 | Lanois et al. |
| 2015/0265327 A1 | 9/2015 | Berg |
| 2015/0374356 A1 | 12/2015 | Hernandez |
| 2016/0058551 A1 | 3/2016 | ElAttrache et al. |
| 2016/0095588 A1 | 4/2016 | ElAttrache et al. |
| 2016/0157852 A1 | 6/2016 | Dougherty et al. |
| 2016/0235399 A1 | 8/2016 | Housman et al. |
| 2016/0302785 A1 | 10/2016 | Nason et al. |
| 2016/0310260 A1 | 10/2016 | Sengun et al. |
| 2016/0317162 A1 | 11/2016 | Dougherty et al. |
| 2016/0367357 A1 | 12/2016 | Dougherty et al. |
| 2016/0374661 A1 | 12/2016 | Housman et al. |
| 2017/0042530 A1 | 2/2017 | Lombardo et al. |
| 2018/0256149 A1 | 9/2018 | Gustafson et al. |
| 2022/0175366 A1* | 6/2022 | Huang ............... A61B 17/0401 |
| 2023/0218288 A1* | 7/2023 | Padilla ............... A61B 17/0401 |
| | | 606/232 |

FOREIGN PATENT DOCUMENTS

| | | |
|---|---|---|
| WO | WO-2011060022 A2 | 5/2011 |
| WO | WO-2012129388 A1 | 9/2012 |
| WO | WO-2014014797 A1 | 1/2014 |
| WO | WO-2017023883 A1 | 2/2017 |

\* cited by examiner

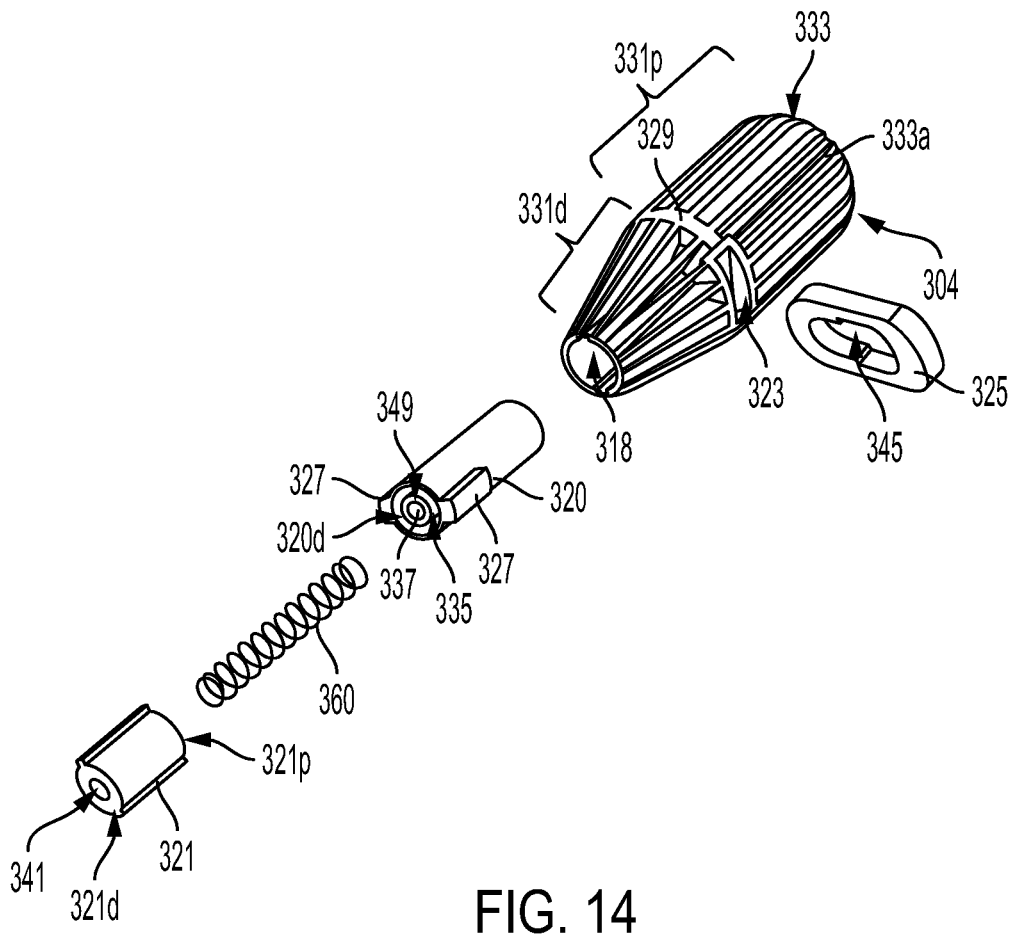
FIG. 14
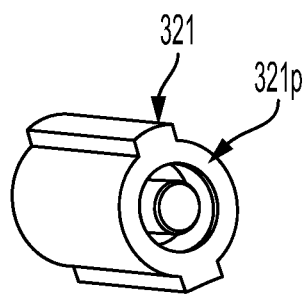
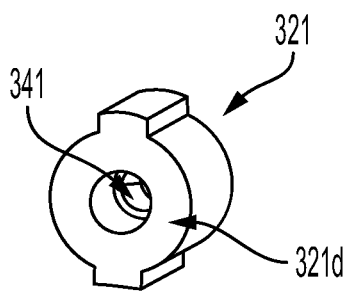
FIG. 15A  FIG. 15B

KNOTLESS SUTURE ANCHORING USING TWO AWL SHAFTS

CROSS REFERENCE TO RELATED APPLICATIONS

This application is a continuation of U.S. patent application Ser. No. 16/709,634 (now U.S. Pat. No. 11,497,483), filed on Dec. 10, 2019, and entitled "Knotless Suture Anchoring Using Two Awl Shafts," which is a divisional of U.S. patent application Ser. No. 15/661,901 (now U.S. Pat. No. 10,639,026), filed on Jul. 27, 2017, and entitled "Knotless Suture Anchoring Using Two Awl Shafts," which are hereby incorporated by reference in their entireties.

FIELD

The present disclosure relates generally to methods and devices for securing tissue to bone.

BACKGROUND

Tearing of, or complete or partial detachment of ligaments, tendons and/or other soft tissues from their associated bones within the body are commonplace injuries. Such injuries can result from excessive stresses being placed on these tissues. By way of example, tissue tearing or detachment may occur as the result of an accident such as a fall, over-exertion during a work-related activity, or during the course of an athletic event. In the case of tearing or a partial or complete detachment of soft tissue from a bone, surgery is typically required to reattach the soft tissue (or a graft tissue) to the bone.

Numerous devices have been used to secure soft tissue to bone. Examples of such devices include screws, tacks, staples, suture anchors, and suture alone. In soft tissue repair or re-attachment procedures utilizing suture anchors, an anchor-receiving hole is drilled into bone at the desired point of fixation or tissue re-attachment, and a suture anchor is deployed into the hole using an appropriate installation tool. A suture, coupled to the suture anchor and passed through or around the soft tissue, thus becomes effectively locked to the bone, which secures the soft tissue to the bone.

During a suture anchoring procedure, it can be challenging to deploy the suture anchor into the anchor-receiving hole. Further, existing suture anchors and inserter devices used to insert the anchors into bone may have certain disadvantages that complicate their use and/or impose certain undesirable limits. Also, procedures that require the suture to be tied into a knot can be time-consuming and cumbersome due to inherent space constraints, which can complicate a surgery.

Accordingly, there is a need for improved methods and systems for attaching tissue to bone.

SUMMARY

In one aspect, a surgical system is provided that in some embodiments includes a driver having a proximal handle and a driver shaft extending therefrom, a distal awl shaft and a proximal awl shaft separate from the distal awl shaft and movable proximally with respect to the distal awl shaft, and a suture anchor. The driver has a lumen extending therethrough, and the distal and proximal awl shafts can be receivable in the lumen of the driver such that a portion of the distal awl shaft extends distally from a distal end of the driver shaft and the proximal awl shaft is disposed proximally to the distal awl shaft. The suture anchor can have a lumen extending therethrough that removably receives the distal awl shaft, wherein a distal driver feature of the driver shaft is operably coupled to the suture anchor.

The system can vary in numerous ways. For example, the driver shaft can have a suture retaining feature extending longitudinally through a sidewall thereof and communicating with a suture retaining feature of the distal awl shaft extending longitudinally through a sidewall of the distal awl shaft. In some embodiments, the suture retaining feature of the distal awl shaft can be configured to receive at least one suture therethrough such that the suture received therethrough extends proximally through the suture anchor and through at least a portion of the suture retaining feature of the driver shaft.

In at least some embodiments, the proximal awl shaft can be a solid elongate member. In some embodiments, the system can further include a suture holding feature coupled to an outer wall of the driver shaft proximal to a distal end of the suture retaining feature of the driver shaft. In at least some embodiments, the suture holding feature can extend at least partially radially about the outer wall of the driver shaft.

In some embodiments, a distal end of the proximal awl shaft abuts a proximal end of the distal awl shaft in a configuration in which the system is used to form a hole in a bone. The distal end of the proximal awl shaft can be spaced apart from the proximal end of the distal awl shaft in a configuration in which the system is used to drive the suture anchor into the hole. In some embodiments, the proximal end of the distal awl shaft has a mating feature having a diameter that is greater than a diameter of a portion of the distal awl shaft extending from the mating feature. The distal end of the proximal awl shaft can abut the proximal end of the distal awl shaft such that, in the configuration in which the system is used to form the hole in the bone, the driver shaft is prevented from being driven distally relative to the distal awl shaft.

In some embodiments, the proximal awl shaft can have an awl handle coupled to a proximal portion thereof, the awl handle being configured to be activated to cause the proximal awl shaft to be retracted proximally away from the distal awl shaft. The awl handle can vary in many ways. For example, the awl handle can be disposed at least partially within the proximal handle of the driver, and the awl handle and the proximal handle of the driver can be independently movable. In some embodiments, the awl handle can have a trigger feature configured to be activated to cause the proximal awl shaft to be retracted proximally away from the distal awl shaft.

The driver can have various configurations. For example, the distal drive feature of the driver can have a hexagonal cross section.

In some embodiments, the surgical system can include a dilator feature that is distal to the suture anchor. The dilator feature can have a distal portion of the distal awl shaft at least partially extending therethrough such that at least a portion of a distal tip of the distal awl shaft extends distally from a distal end of the dilator feature.

In another aspect, a method of performing a surgical repair is provided that in some embodiments includes advancing a distal end of a distal awl shaft into a bone to form a bone hole, a proximal end of the distal awl shaft abutting a distal end of a proximal awl shaft such that the proximal awl shaft applies a load to the proximal end of the distal awl shaft. The method further includes, after the bone hole has been formed, moving the proximal awl shaft to a retracted configuration such that the distal end of the proximal awl shaft is spaced apart from the proximal end of the distal awl shaft. With the proximal awl shaft in the retracted configuration, the method can further include driving a suture anchor having a suture coupled thereto distally into the bone hole and thereby securing the suture between an inner wall of the bone hole and an outer surface of the suture anchor.

The method can have a number of variations. For example, moving the proximal awl shaft to the retracted configuration can include activating a handle coupled to a proximal portion of the proximal awl shaft. As another example, in some embodiments, the distal awl shaft can extend through an implantable dilator feature, through the suture anchor positioned proximal to the dilator feature, and through a portion of a driver shaft, wherein driving the suture anchor distally into the bone hole comprises driving the suture anchor distally towards the dilator feature. As a further example, the method can include applying tension on a terminal end portion of the suture while the proximal awl shaft is moved to the retracted configuration.

In some embodiments, the terminal end portion of the suture can be passed through a suture retaining feature of the distal awl shaft, through a lumen of the suture anchor, and through at least a portion of a suture retaining feature of the driver shaft, the terminal end portion extending from the driver shaft.

BRIEF DESCRIPTION OF THE DRAWINGS

The present disclosure will be more fully understood from the following detailed description taken in conjunction with the accompanying drawings, in which:

FIG. 14 is a perspective, exploded view of a proximal handle of the surgical system of FIG. 13A;

FIG. 15A is a perspective, proximal view of a driver shaft holder of the surgical system of FIG. 14;

FIG. 15B is a perspective, distal view of the driver shaft holder of the surgical system of FIG. 14;

DETAILED DESCRIPTION

Figure 1:
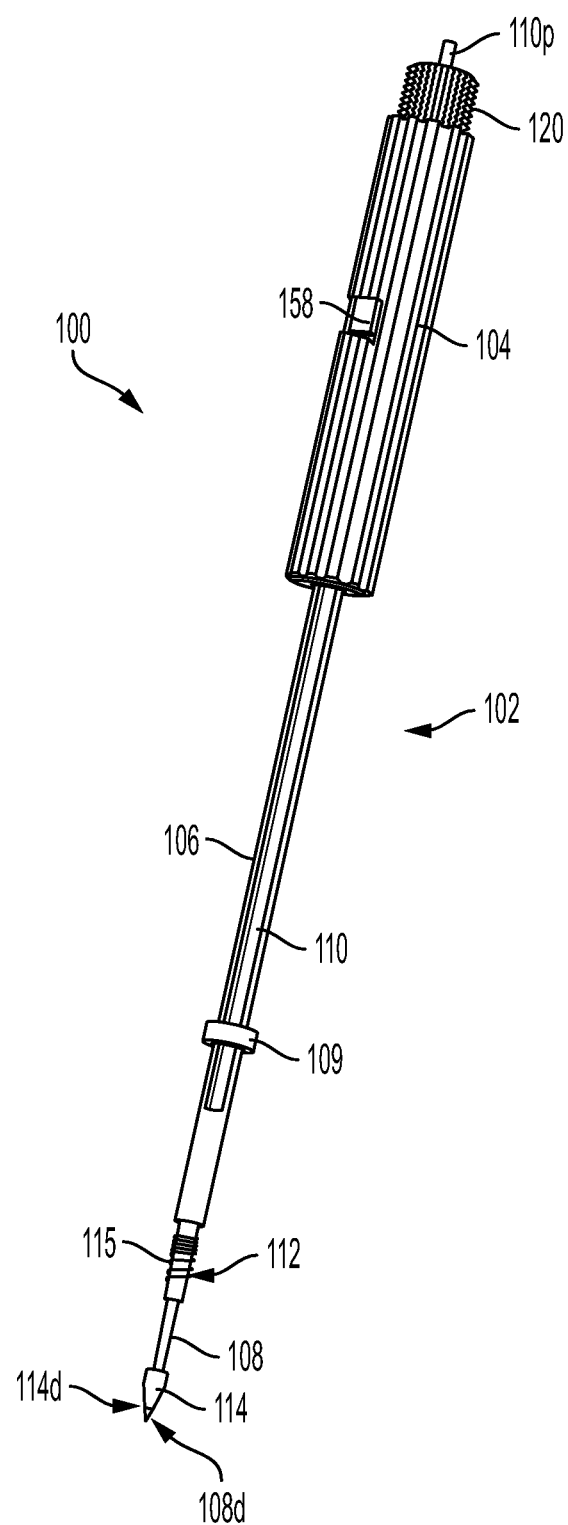
FIG. 1 is a perspective view of one embodiment of a surgical system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various methods and devices are provided for securing tissue to bone. In at least some of the described embodiments, a surgical system is provided that can include a driver device or driver, a distal awl shaft, a proximal awl shaft, and a suture anchor. The driver can have a proximal handle and a driver shaft extending therefrom, the driver shaft having a lumen extending therethrough. The proximal awl shaft is separate from the distal awl shaft and is movable proximally with respect to the distal awl shaft. The distal and proximal awl shafts can be receivable in the lumen of the driver such that a portion of the distal awl shaft extends distally from a distal end of the driver shaft and the proximal awl shaft is disposed within the lumen of the driver. The suture anchor has a lumen extending therethrough that removably receives the distal awl shaft. A distal driver feature of the driver shaft is operably coupled to the suture anchor such that the driver shaft can be rotated to cause the suture anchor to be driven distally into a bone. In some embodiments, the surgical system can also include a dilator feature distal to the suture anchor. The dilator feature can have a distal portion of the distal awl shaft at least partially extending therethrough such that at least a portion of a distal tip of the distal awl shaft extends distally from a distal end of the dilator feature.

In the illustrated embodiments, the surgical system can have a first configuration in which the system is used to form a bone hole and a second configuration in which the system is used to drive a suture anchor into the bone hole. In the first, bone hole forming configuration, a distal end of the proximal awl shaft abuts a proximal end of the distal awl shaft. In this way, when the surgical system is driven into a bone by applying a load to its proximal end (e.g., by using a mallet or other suitable instrument), the proximal awl shaft applies a load to the distal awl shaft. Also, in this configuration, the driver shaft can be prevented from moving distally relative to the distal awl shaft. After the system has been used to form a bone hole, as discussed in more detail below, the proximal awl shaft can be retracted proximally such that the distal end of the proximal awl shaft becomes spaced apart from the proximal end of the distal awl shaft. For example, an awl handle coupled to a proximal portion of the proximal awl shaft can be operated to cause the proximal awl shaft to be moved proximally. Once the proximal awl shaft has been moved proximally, the surgical system can be used to drive the suture anchor into the bone.

FIGS. 1-11 and 12A-12D illustrate one embodiment of a surgical system 100 that includes a driver device or driver 102 having a proximal handle 104 and a driver shaft 106 extending therefrom, a distal awl shaft 108, a proximal awl shaft 110 that is separate from the distal awl 108, a suture anchor 112, and a dilator feature 114 that can be implantable. The system 100 also includes an awl handle 120 coupled to the proximal awl shaft 110 and extending at least partially proximally from the proximal handle 104, as shown in FIG. 1. The driver shaft 106 can have a lumen 116 extending longitudinally therethrough, as shown in FIG. 5. The lumen 116 of the driver shaft 106 is configured to receive at least partially therethrough the distal awl shaft 108 such that a portion of the distal awl shaft 108 extends distally from a distal end of the driver shaft 106 and the proximal awl shaft 110 is disposed within the lumen 116 proximal to the distal awl shaft 108, as also shown in FIG. 5.

The proximal handle 104 has a lumen 118 extending along a length thereof and communicating with the lumen 116 of the driver shaft 106. The lumen 116 of the driver shaft 106 and the lumen 118 of the proximal handle 104 provide a lumen that is configured to receive the proximal awl shaft 110 therethrough, as shown in FIGS. 1, 4, 6A, and 6B. A proximal end 110p of the proximal awl shaft 110 can protrude proximally from the proximal end of the awl handle 120. However, in other embodiments, the proximal end 110p may not protrude from the proximal end of the awl handle 120. As shown in FIG. 1, the surgical system 100 has a suture holding feature 109 coupled to an outer wall of the driver shaft 106.

The suture anchor 112, which can have external threads 115 formed thereon, has a lumen 113 extending therethrough that removably receives the distal awl shaft 108. A distal driver feature of the driver shaft 106 is operably coupled to the suture anchor, as discussed in more detail below. The dilator feature 114, which is distal to the suture anchor 112, has a distal portion of the distal awl shaft 108 at least partially extending therethrough such that at least a portion of a distal tip 108d of the distal awl 108 shaft extends distally from a distal end 114d of the dilator feature 114, as shown, for example, in FIGS. 1, 4 and 5. It should be appreciated that a dilator feature may not be present in some implementations.

Figure 4:
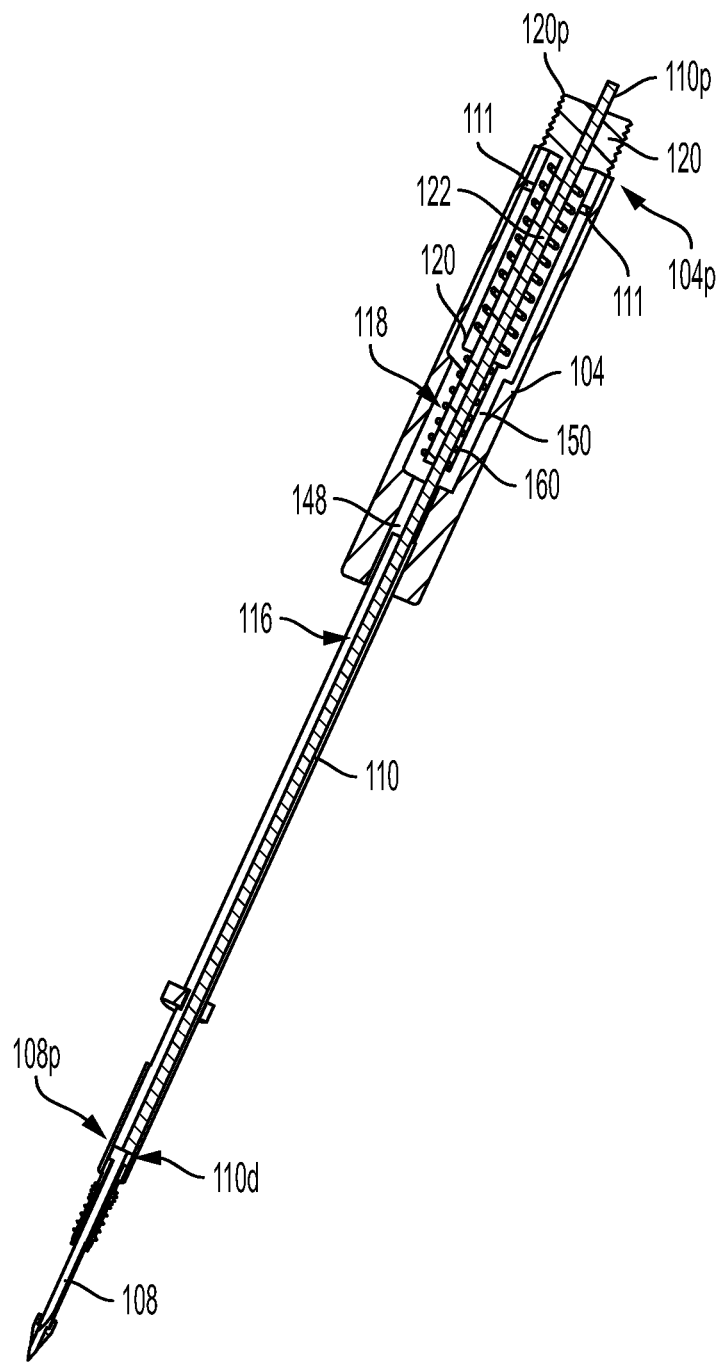
FIG. 4 is a side cross-sectional view of the surgical system of FIG. 1, showing the surgical system in a bone hole forming configuration.
Figure 5:
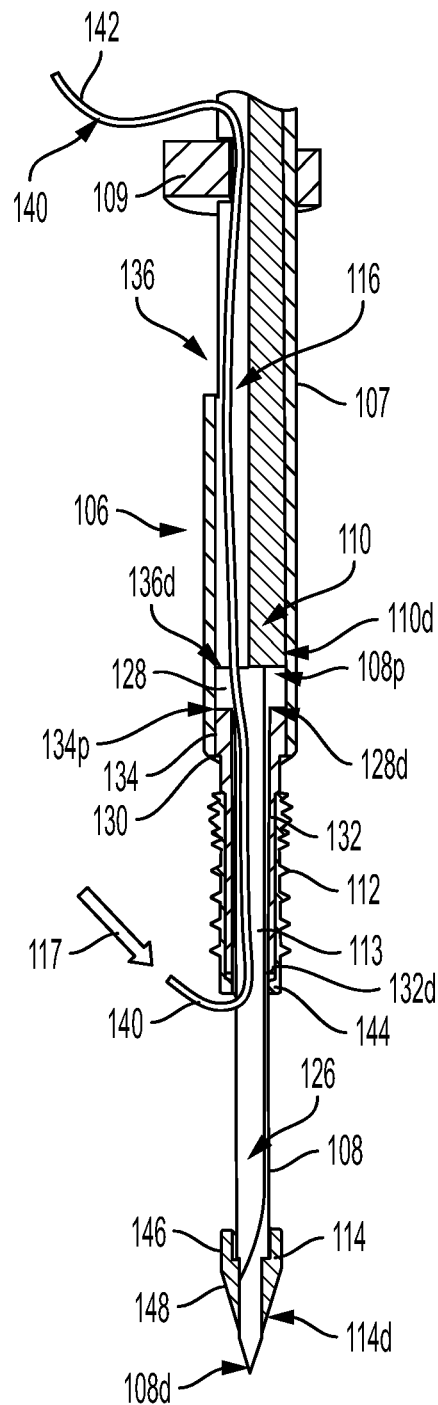
FIG. 5 is a perspective, partially cross-sectional view of a distal portion of the surgical system of FIG. 1, showing the surgical system in a bone hole forming configuration.

As shown in FIG. 4, the proximal awl shaft 110 has the awl handle 120 coupled to a proximal portion thereof such as, for example, the portion of the proximal awl shaft 110 extends through a bore in the awl handle 120. The proximal awl shaft 110 is non-movably coupled to the awl handle 120 that is configured to be activated to cause the proximal awl shaft 110 to be retracted proximally away from the distal awl shaft 108. In the illustrated embodiment, the awl handle 120 is disposed at least partially within the proximal handle 104 of the driver 102, and the awl handle 120 and the proximal handle 104 of the driver 102 can be independently movable, as discussed in more detail below. The proximal awl shaft 110 can be coupled to the awl handle 120 in many various ways, for example, by press-fit, by adhesive, glue, by ultrasonic welding, etc.

Figure 2:
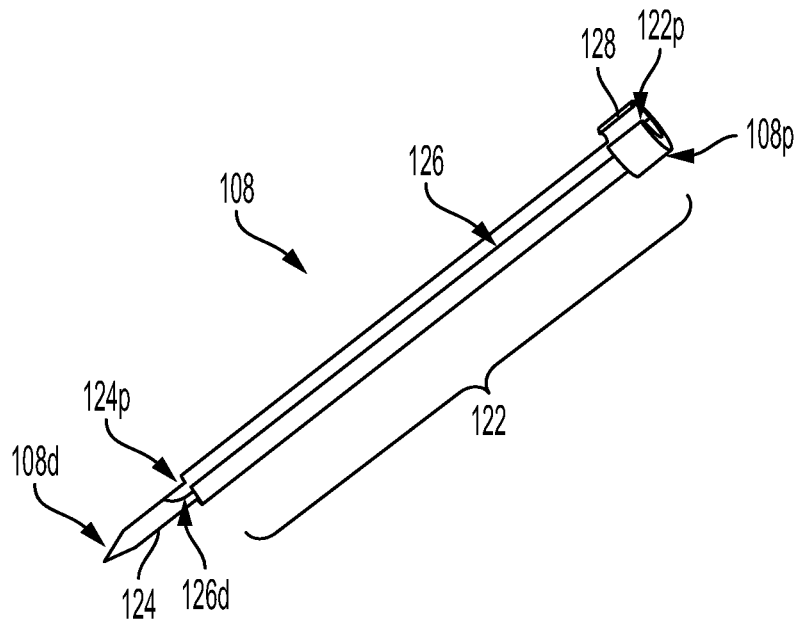
FIG. 2 is a perspective view of a distal awl shaft of the surgical system of FIG. 1.

The components of the system 100 can have various configurations. Thus, the distal and proximal awl shafts 108, 110 can have many variations. As shown in FIGS. 2, 4, and 5, the distal awl shaft 108 is a generally cylindrical elongate member having a central portion 122 and a distal portion 124 extending distally from the central portion 122. At least a portion of the distal awl shaft 108 can have a suture retaining feature 126 extending longitudinally through a sidewall thereof. For example, in the illustrated embodiment, the suture retaining feature 126 extends from (and through) a portion of a proximal end 124p of the distal portion 124 to a proximal end 122p of the central portion 122, which coincides with a proximal end 108p of the distal awl shaft 108. As shown in FIG. 2, the suture retaining feature 126 has a proximal opening at the proximal end 108p of the distal awl shaft 108. As also shown in FIG. 2, in the illustrated embodiment, a distal end 126d of the suture retaining feature 126 is disposed just distal to the proximal end 124p of the distal awl shaft's distal portion 124.

In some embodiments, the proximal end of the distal awl shaft 108 can have a larger diameter than a distal end of the proximal awl shaft 110. In the illustrated embodiment, the proximal end 108p of the distal awl shaft 108 includes a mating feature 128 having a diameter that is greater than a diameter of a portion of the distal awl shaft extending from the mating feature. In particular, as shown in FIG. 2, the diameter of the mating feature 128 is greater than the diameter of the rest of the central portion 122 of the distal awl shaft 108. As also shown in FIG. 2, the distal portion 124 of the distal awl shaft 108 has a diameter that is less than the diameter of the central portion 122.

Figure 3:
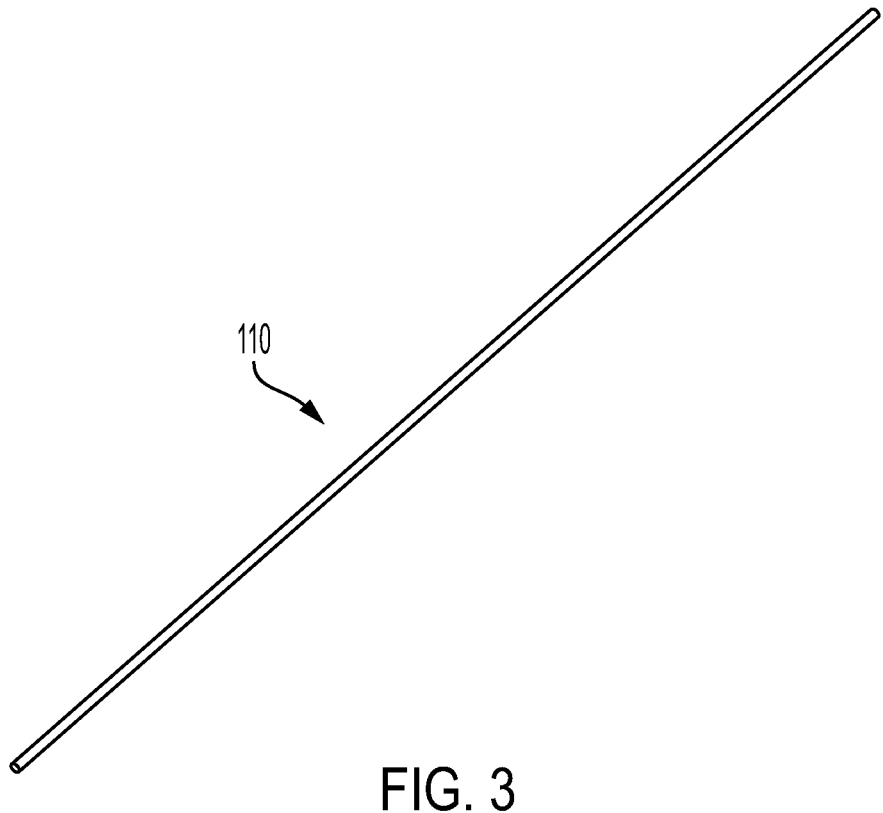
FIG. 3 is a perspective view of a proximal awl shaft of the surgical system of FIG. 1.

As shown in FIGS. 3-5, the proximal awl shaft 110 can be a generally cylindrical elongate member. The proximal awl shaft 110 extends through the lumen 116 of the driver 102 such that a proximal end 110*p* the proximal awl shaft 110 extends from a proximal end 120*p* of the awl handle 120. The system 100 is used to initiate a hole in bone and, once the bone hole is formed, to drive the suture anchor into the hole. In the illustrated embodiments, as shown in FIGS. 4 and 5, a distal end 110*d* of the proximal awl shaft 110 abuts the proximal end 108*p* of the distal awl shaft 108 in a configuration in which the system 100 is used to form a hole in a bone. The system 100 can be configured such that, in the bone hole forming configuration, the proximal awl shaft 110 is biased against the distal awl shaft 108 such that the driver shaft 106 is prevented from being moved distally relative to the distal awl shaft 108.

When load is applied to the proximal awl shaft 110 during initiation of the hole, the proximal awl shaft 110 applies load to the distal awl shaft 108 the distal end 108*d* of which is inserted into the bone. Thus, the distal and proximal awl shafts 108, 110 act together to allow the system 100 to operate as a self-punching shaft used to initiate a hole in the bone. Thus, no additional instruments may be required to initiate the hole. Once the hole in the bone is initiated, the distal end 108*d* of the distal awl shaft 108 can be driven further distally into the hole by further applying load to the proximal awl shaft 110. The dilator feature 114, which can be implantable, can assist in widening the hole in the bone as the hole is being formed.

Figure 6A:
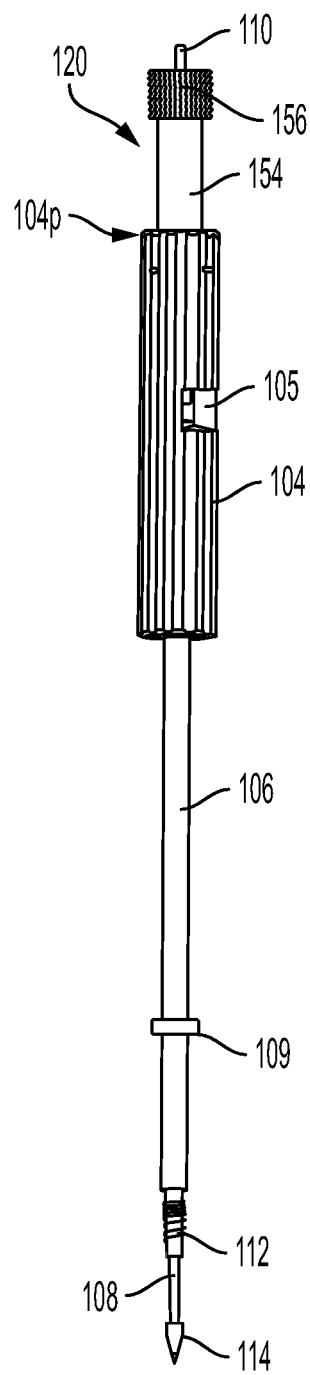
FIG. 6A is a perspective view of the surgical system of FIG. 1, showing the surgical system in a suture anchor insertion configuration.
Figure 6B:
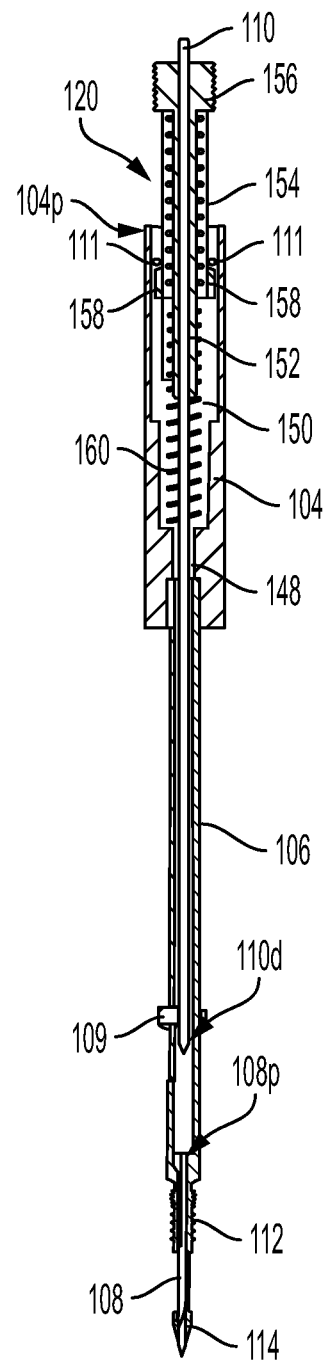
FIG. 6B is a side cross-sectional view of the surgical system of FIG. 6A.

Once the bone hole is formed, the proximal awl shaft 110 is retracted proximally from the distal awl shaft 108, for example, by activating the awl handle 120 coupled to the proximal awl shaft 110 as shown in FIGS. 6A and 6B which are discussed in more detail below. The distal end 108*d* of the distal awl shaft 108 remains in the bone hole and the suture anchor 112 can be driven over the distal awl shaft 108 without being hindered by the proximal awl shaft 110. Also, moving the proximal awl shaft 110 such that its distal end 110*d* is spaced apart from the proximal end 108*p* of the distal awl shaft 108 allows the proximal awl shaft 110 to be out of the way of the suture when the suture anchor 112, having the suture coupled thereto, is driven into the bone. This configuration avoids a possibility of the suture wrapping around the proximal awl shaft during insertion of the suture anchor, which could occur when a one-piece awl shaft is used instead of the distal and proximal awl shafts described herein.

Figure 7:
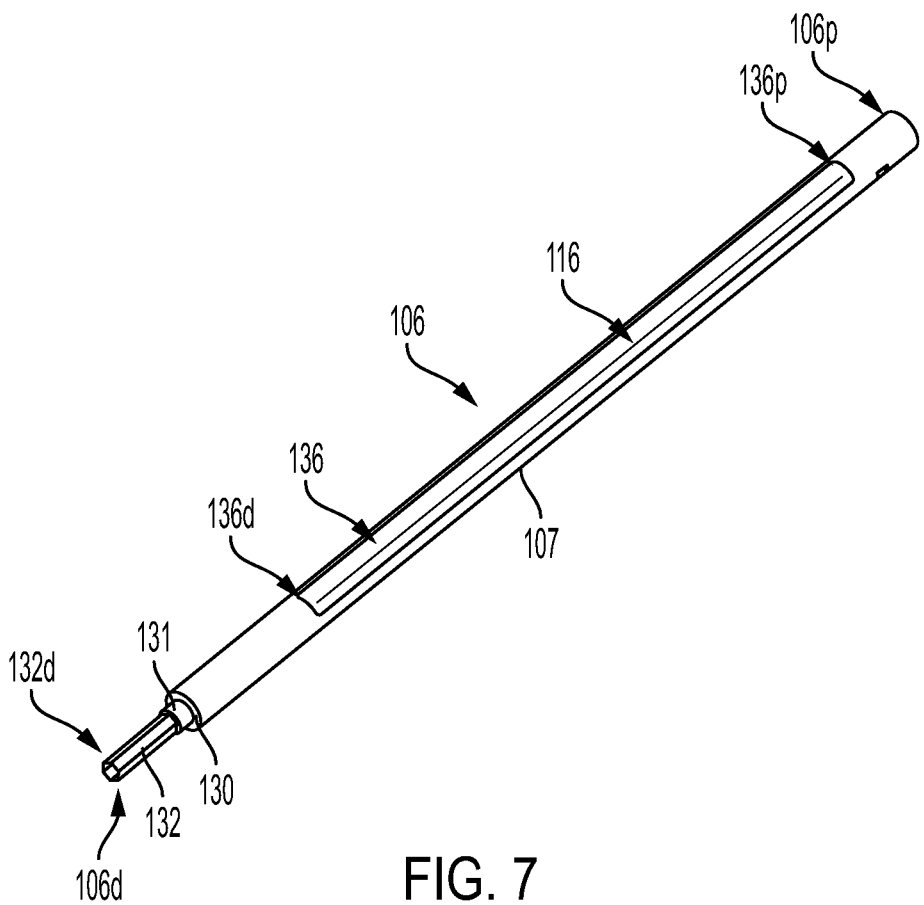
FIG. 7 is a perspective view of a driver shaft of a driver of the surgical system of FIG. 1.
Figure 8:
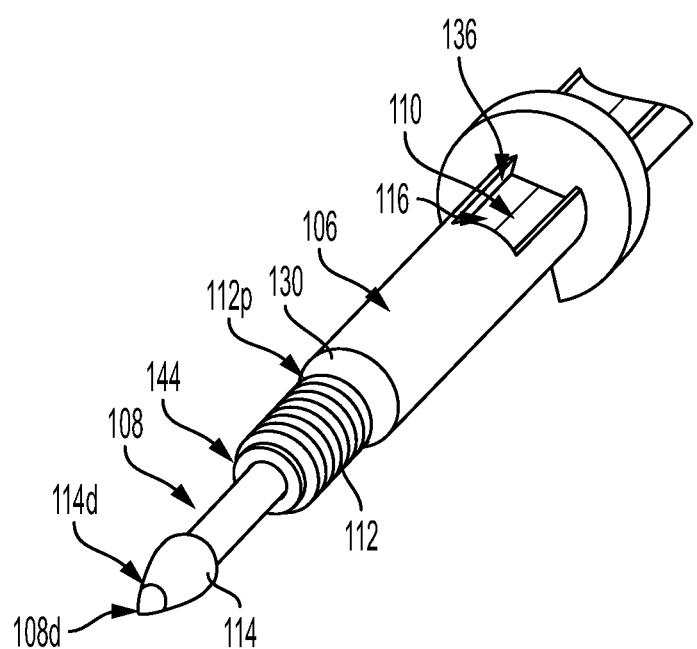
FIG. 8 is a perspective view of a distal portion of the surgical system of FIG. 1.

The driver 102 that is configured to drive the suture anchor 112 into bone can have various configurations. The driver shaft 106 can be coupled to the proximal handle 104 in various ways. As shown in FIG. 7, the driver shaft 106 has a central portion 107 having a shoulder 130 at a distal surface thereof. The shoulder 130 is proximal to a distal driver member 132 that extends from the shoulder 130 to a distal end 132*d* of the distal driver member 132. The distal end 132*d* is also a distal end 106*d* of the driver shaft 106 of the driver 102. The distal driver member 132 has the suture anchor 112 mounted thereon. In the illustrated embodiment, the driver shaft 106 has a neck feature 131 disposed between the shoulder 130 and the distal driver member 132 such that the neck feature 131 abuts a proximal end 112*p* of the suture anchor 112. In use, the neck feature 131 facilitates driving the suture anchor 112 distally. It should be appreciated that the driver shaft 106 can have other suitable configurations, including the configurations in which the shoulder 130 and/or the neck feature 131 are not included.

The lumen 116 of the driver shaft 106 receives the distal awl shaft 108 such that a proximal portion of the distal awl shaft 108 is seated within the lumen 116. For example, as shown in FIG. 5, the distal awl shaft 108 is received within the driver shaft's lumen 116 such that the mating feature 128 of the distal awl shaft 108 is seated proximal to the distal driver feature 132 of the driver shaft 106. A distal surface 128*d* of the mating feature 128 abuts a proximal surface 134*p* of an inner shoulder 134 disposed within the driver shaft's lumen 116 proximal to the shoulder 130 of the driver 102.

Further, in the illustrated embodiment, the driver shaft 106 of the driver 102 has a suture retaining feature 136 extending longitudinally through a sidewall thereof. The suture retaining feature 136, which can be in the form of a slot, communicates with the suture retaining feature 126 of the distal awl shaft 108, as shown, for example, in FIG. 5. In the illustrated embodiment, the suture retaining feature 136 of the driver shaft 106 can be in the form of a longitudinal slot that opens into the lumen 116 of the driver shaft 106. As shown in FIG. 7, the suture retaining feature 136 extends along the length of the driver shaft 106 between its distal and proximal ends 136*d*, 136*p*. In this example, the distal end 136*d* of the suture retaining feature 136 is proximal to the shoulder 130 and the proximal end 136*p* is distal to the proximal end 106*p* of the driver shaft 106. It should be appreciated that the suture retaining feature 136 can be formed in other ways in the driver shaft 106.

As shown in FIG. 5, a suture 140 (which can be in the form of two or more suture strands) can be passed as shown by arrow 117—such that suture's terminal end portion 142 is passed through the suture retaining feature 126 of the distal awl shaft 108, through the lumen 113 of the suture anchor 112 (which has the distal awl shaft 108 extending therethrough) and through at least a portion of the suture retaining feature 136 of the driver shaft 106. The terminal end portion 142 of the suture 140 extends from the driver shaft 106 as shown in FIG. 5. As also shown, the terminal end portion 142 extends from the driver shaft 106 proximally to the suture holding feature 109 coupled to the outer wall of the driver shaft 106 proximal to the distal end 136*d* of the suture retaining feature 136 of the driver shaft 106. The suture holding feature 109 which can, for example, extend at least partially radially about the outer wall of the driver shaft 106, allows, in use, maintaining a position of the suture 140 while preventing suture wrapping within the driver shaft 106. Also, in an arthroscopic procedure, the suture holding feature 109 facilitates directing the terminal end 142 of the suture 140 out of a cannula through which the system 100 (and other instruments) can be inserted to access a surgical site.

The suture holding feature 109 can have various configurations and it be coupled to the driver shaft 106 in a variety of ways. For example, the suture holding feature 109 can be in the form of a ring, or it can have a semi-circular shape. It can be non-movably attached to the driver shaft 106. In some embodiments, however, the suture holding feature 109 can be movable with respect to the driver shaft 106, though it is coupled to the driver shaft 106 such that its position with respect to the shaft 106 can be adjustable. For example, the suture holding feature 109 can be configured to be slidably attached to the driver shaft 106, e.g., via friction fit or in other ways, such as a position of the suture holding feature 109 with respect to the driver shaft 106 can be adjusted and, once adjusted, maintained. The suture holding feature 109 can be attached to the driver shaft 106 removably or, in some implementations, it can be permanently fixed to the shaft driver shaft. In at least one embodiment, the suture holding feature 109 can have an opening on a side thereof such that the feature 109 can be snapped on or otherwise removably coupled to the driver shaft 106.

The suture holding feature 109 can be coupled to the driver shaft 106 such that the suture holding feature 109 seats above a cannula which can be used in a surgical procedure. For example, in use, the system 300 can be inserted to a surgical site through the cannula, and the suture holding feature 109 can then be slidably or otherwise attached to the driver shaft 106.

The suture anchor 112 can have various configurations. In the illustrated embodiment, as mentioned above, the suture anchor 112 has at least one external thread 115 formed thereon that is configured to engage the suture anchor 112 with the bone. However, the suture anchor 112 can have any suitable configuration and can have other bone-engaging features. For example, in some embodiments, the suture anchor can be a screw-in anchor. In some embodiments, the suture anchor can be a push-in style suture anchor.

Figure 9:
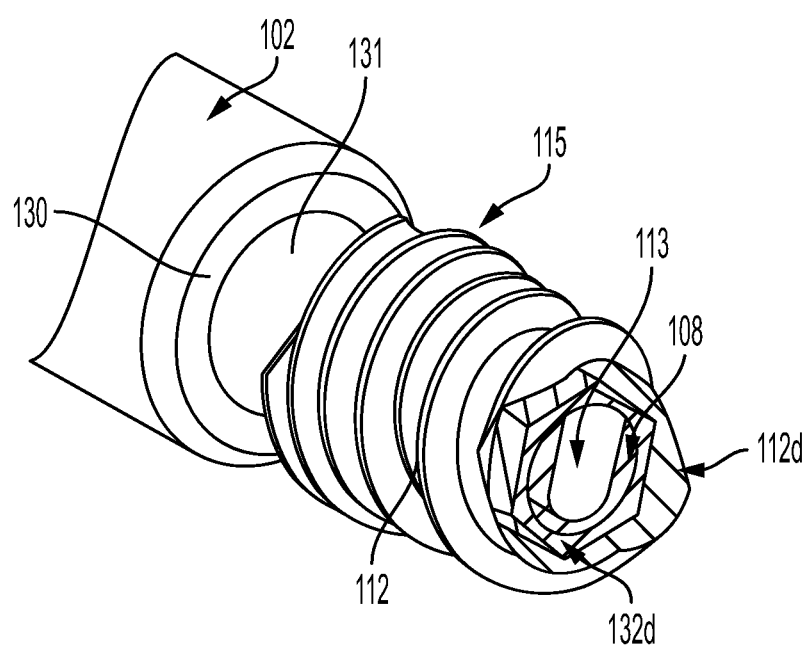
FIG. 9 is a perspective, partially cross-sectional view of a distal portion of the surgical system of FIG. 1, also showing a cross-sectional view of a suture anchor.

As shown in FIG. 9, the suture anchor 112 has the lumen 113 extending therethrough such that at least a portion of the lumen 113 can receive therein the distal driver member 132. In an assembled configuration, as shown in FIGS. 5 and 9, the distal driver member 132 extends through the lumen 113 of the suture anchor 112 such that the distal end 132d of the distal driver member 132 is disposed proximal to a distal end 112d of the suture anchor 112. However, in other embodiments, the distal end 132d of the distal driver member 132 can be aligned with or can extend beyond the distal end 112d of the suture anchor 112. As shown in FIG. 9, the lumen 113 of the suture anchor 112 also receives therethrough the distal awl shaft 108 that extends through the distal driver member 132.

The distal driver member 132 of the driver 102 is configured to releasably mate with the suture anchor 112 and to thereby drive the suture anchor 112 mated thereto distally into bone (over the distal awl shaft 108), as discussed in more detail below. In some embodiments, as illustrated herein, the distal driver member 132 can be in the form of a male feature configured to be received within a corresponding female drive feature formed on at least a portion of an interior wall defining the lumen of the suture anchor 112.

In the illustrated embodiment, as shown in FIG. 9, the distal driver member 132 can be in the form of a male feature that is hexagonal-shaped, and the corresponding female drive feature of the suture anchor 112 can be a corresponding hexagonal-shaped female drive feature formed in at least a portion of an interior wall defining the lumen 113 of the suture anchor 112. FIG. 9 shows that at least a portion of the interior wall defining the lumen 113 of the suture anchor 112 is hexagonal in cross-section. In the illustrated embodiment, a distal portion 144 (FIGS. 5 and 8) of the interior wall defining the suture anchor's lumen 113 may be circular in cross-section such that it does not have the hexagonal feature. In this embodiment, the distal driver member 132 of the driver 102 extends through the lumen 113 of the suture anchor 112 such that the distal end 132d of the distal driver member 132 is disposed proximal to the distal end 112d of the suture anchor 112. The distal portion 144 of the interior wall defining the lumen 113 of the suture anchor 112 is circular in cross-section, which facilitates passage of a suture through a distal end of the lumen 113 of the suture anchor 112. The circular cross-sectional shape of the distal portion 144 of the lumen 113 also helps prevent suture tangling around the distal end of the suture anchor 112.

In the illustrated embodiment, as shown in FIGS. 1, 4, 5, 6A, 6B, and 8, the surgical system 100 includes the dilator feature 114 that is distal to the suture anchor 112. The distal awl shaft 108 is configured to extend through a lumen of the dilator feature 114 such that the distal end 108d of the distal awl shaft 108 extends distally from the dilator feature 114, as shown, for example, in FIG. 8. The dilator feature 114 is configured to facilitate insertion of the distal awl shaft 108 into bone by widening a hole in bone once the hole is initiated, such as by the distal end 108d of the distal awl shaft 108. The dilator feature 114 can be distally tapered and it can be in the form of a truncated cone or pyramid. In the illustrated example, as shown in FIG. 4, the dilator feature 114 can have a proximal neck portion 146 that has substantially the same diameter along its length, and a distal portion 148 that extends distally from the proximal neck portion 146 and that is distally tapered. An outer wall of the distal portion 148 of the dilator feature 114 can be conical without any surface features. In some embodiments, however, at least a portion of the dilator feature can have two or more faces, which can be, for example, triangular. For example, in one embodiment, the dilator feature can have three faces. The faces can be substantially flat or they can have other configurations and features that facilitate insertion of the dilator feature into bone. It should be appreciated that the dilator feature 114 can have any suitable configurations.

The dilator feature 114 can be press-fit onto or otherwise releasably coupled with the distal awl shaft 108 and it can have any suitable dimensions. Furthermore, in some embodiments, the dilator feature 114 can be implantable and it can be made from a non-metallic material. This can be beneficial since the properties of non-metallic materials are such that they would not interfere with post-implantation imaging of the repair done using the system 100. Moreover, while it is sufficiently rigid to assist in forming a bone hole, the dilator feature 114 can be bioabsorbable and/or biodegradable. However, in other embodiments, the dilator feature 114 can be made from a metal.

Figure 10:
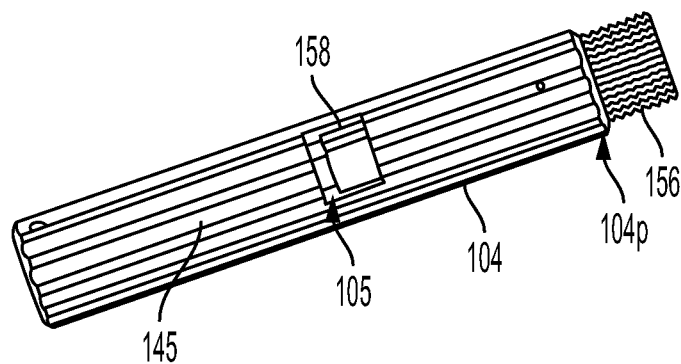
FIG. 10 is a perspective view of a proximal handle of the surgical system of FIG. 1, the proximal handle having an awl handle associated therewith.

The proximal handle 104 of the driver 102 can have a variety of configurations. In the illustrated embodiment, as shown in FIGS. 4 and 6B, the lumen 118 of the proximal handle 104 receives a proximal portion of the driver shaft 106 such that the lumen 118 communicates with the lumen 116 of the driver shaft 106. In this way, the lumens 116 and 118 receive the proximal awl shaft 110 therethrough. The driver shaft 106 is coupled to the proximal handle 104 in any suitable manner, such that rotation of the proximal handle 104 causes the driver shaft 106 to be rotated. The proximal handle 104 of the driver 102 can be configured to have surface features that facilitate grip during use of the system 100. For example, as shown in FIG. 10, the proximal handle 104 has one or more grooves 145 formed along its length. It should be appreciated, however, that the proximal handle 104 can have any suitable surface features, as the described embodiments are not limited in this respect.

The proximal handle 104 of the driver 102 can be coupled to the awl handle 120, which is coupled to the proximal awl shaft 110. For example, as shown in FIGS. 4 and 6B, the lumen 118 of the proximal handle 104 is configured to receive the awl handle 120 at least partially therein. Thus, the lumen 118 of the proximal handle 104 has a distal portion 148 configured to receive the proximal portion of the driver shaft 106, and a proximal portion 150 configured to receive at least part of the awl handle 120 therein. As shown in FIGS. 4 and 6B, the proximal portion 150 of the proximal handle's lumen 118 can have a larger diameter than the distal portion 148 of the lumen 118 and the proximal portion 150 has a configuration corresponding to a configuration of the awl handle 120. The proximal portion 150 of the lumen 118 communicates with openings 105 in the proximal handle 104. As shown in FIGS. 4 and 6B, the proximal portion 150 of the proximal handle's lumen 118 includes pins 111 or other features configured to retain a position of the awl handle 120 (e.g., its tabs 158).

Figure 11:
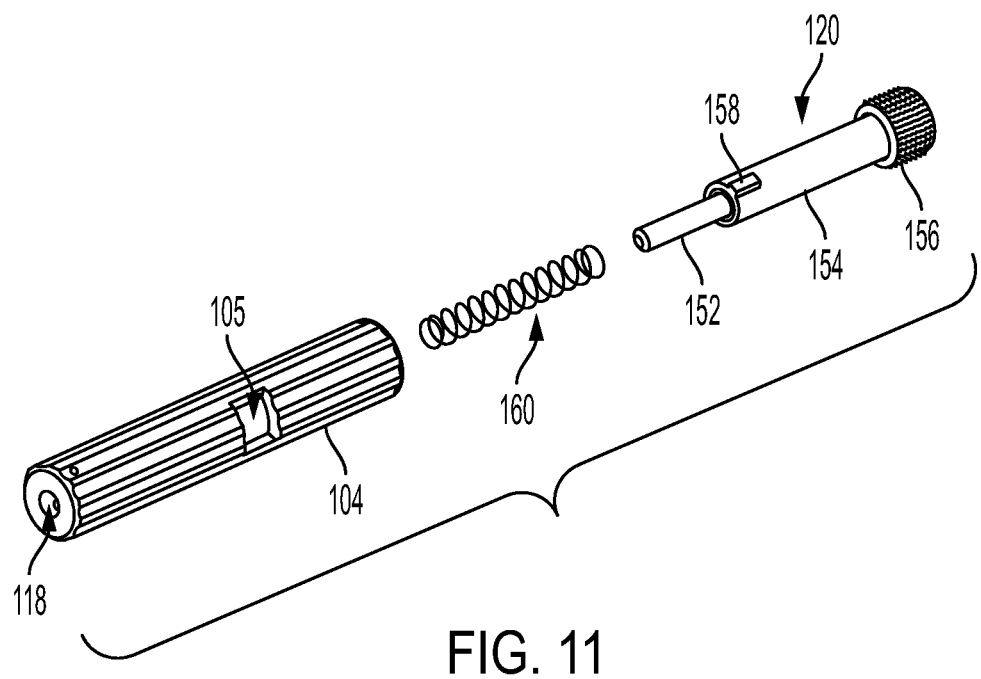
FIG. 11 is a perspective, exploded view of the proximal handle of FIG. 10.

As shown in FIG. 11, the awl handle 120 has a distal portion 152, a central portion 154, and a proximal portion 156. The distal, central, and proximal portions 152, 154, 156 of the awl handle 120 are generally cylindrical, with the distal portion 152 having a diameter smaller than that of the central portion 154, and the central portion 154 having a diameter smaller than a diameter of the proximal portion 156. The distal and central portions 152, 154 of the awl handle 120 are received in the proximal portion 150 of the lumen 118 of the proximal handle 104, and the proximal portion 156 of the awl handle 120 protrudes beyond the proximal end 104p of the proximal handle 104, as shown in FIGS. 4 and 6B. As also shown in FIGS. 4 and 6A, the proximal portion 150 of the lumen 118 can be shaped similarly to the distal and central portions 152, 154 of the awl handle 120 seated therein. Thus, in this example, the proximal portion 150 of the lumen 118 of the proximal handle 104 has a distal part having a diameter that is less than a diameter of a proximal part.

In the illustrated embodiment, the central portion 154 of the awl handle 120 has tabs 158 extending therefrom, as shown in FIGS. 1, 6B, 10, 11, and 12A-12C. The tabs 158 can be in the form of ribs, wings, or they can be any other features. In the bone hole forming configuration of the system 100, the tabs 158 of the of the awl handle 120 protrude from the slots 105 of the proximal handle 104 and thereby prevent the awl handle 120 (and thus the proximal awl shaft 110 coupled there) from moving with respect to the proximal handle 104. In the illustrated embodiment, the proximal portion 150 of the lumen 118 of the proximal handle 104 includes a spring 160 (shown in FIG. 11) configured to bias the awl handle 120 proximally when the awl handle 120 is released from engagement with the proximal handle 104, such as the tabs 158 disengage from the openings 105 in the proximal handle as shown in FIG. 6B. Thus, in the bone hole forming configuration of the system 100, the spring 160, which can extend along a length of the proximal portion 150 of the lumen 118, can be in at least partially compressed configuration.

The proximal portion 156 of the awl handle 120, which is positioned proximal to the proximal end 104p of the proximal handle 104, is configured to be grasped by a user (e.g., a surgeon) to cause the proximal awl shaft 110 to be retracted proximally. The proximal portion 156 can have any suitable surface features that facilitate gripping.

In use, in the configuration in which the system 100 is used to form a hole in bone, the proximal awl shaft 110 is disposed such that its distal end 110d abuts the proximal end 108p of the distal awl shaft 108. In such a configuration, the driver 102 is prevented from being driven distally relative to the distal awl shaft, because of the engagement between the driver's proximal handle 104 and the awl handle 120. To move the system 100 into the configuration in which it can be used to drive the suture anchor into the bone hole, the awl handle 120 can be activated. For example, in the illustrated example, the awl handle 120 can be rotated by grasping and rotating the proximal portion 156 to cause the tabs 158 of the awl handle 120 to rotate and enter the lumen 118 of the proximal handle 104 via the slots 105. In this way, as shown in FIGS. 6A and 6B, once the tabs 158 no longer engage the slots 105 of the proximal handle 104, the awl handle 120, with assistance of the biasing spring 160 disposed in the proximal portion 150 lumen 118 of the proximal handle 104, is caused to move proximally such that the central portion 154 of the awl handle 120 is protruded proximally beyond the proximal end 104p of the proximal handle 104.

As shown in FIG. 6B, the tabs 158 of the awl handle 120 can abut distally the pins 111 in the proximal portion 150 of the proximal handle's lumen 118, thereby the awl handle 120 is prevented from moving further proximally. In this way, the position of the pins 111 within the lumen 118 can determine a distance to which the awl handle 120 is allowed to move proximally. It should be appreciated that in this, as well as in other embodiments described herein, the surgical system can be configured such that a proximal awl shaft can be moved proximally with respect to a distal awl shaft to a predetermined distance. In other words, once the awl handle of the proximal awl shaft is activated, the proximal awl shaft is automatically moved to a desired distance, and no additional action (e.g., by the surgeon) may be required to control how far the proximal awl shaft moves.

When the awl handle 120 is disengaged from the proximal handle 104, the spring 160 can move from the at least partially compressed configuration to the less compressed configuration such that it helps bias the awl handle 120 proximally and to maintain the awl handle 120 in such position.

The proximal movement of the awl handle 120 causes the proximal awl shaft 110, which is coupled thereto, to move proximally away from the distal awl shaft 108. Thus, FIG. 6B illustrates that the distal end 110d of the proximal awl shaft 110 is spaced from the proximal end 108p of the distal awl shaft 108. It should be appreciated that, although FIG. 6B shows the distal end 110d of the proximal awl shaft 110 disposed distal to the suture holding feature 109, in some implementations, the proximal awl shaft 110 can be retracted proximally such that its distal end 110d is disposed proximally to the suture holding feature 109. Also, although not shown in FIGS. 1, 4, 6A, and 6B, in use, the system 100 has a suture coupled thereto, such as shown, for example, in FIG. 5. After the proximal awl shaft 110 is retracted proximally, the proximal handle 104 can be rotated to drive the suture anchor 112 into the bone hole.

FIGS. 12A-12E illustrate a method of performing a surgical repair involving use of a surgical system, such as the surgical system 100 (shown by way of example only), to attach soft tissue 202 (e.g., tendon) to bone 200. It should be appreciated that the surgical repair method in accordance with the described embodiments can be performed using other surgical systems, including surgical systems in which one or more components can be different from those included in the surgical system 100.

Figure 12A:
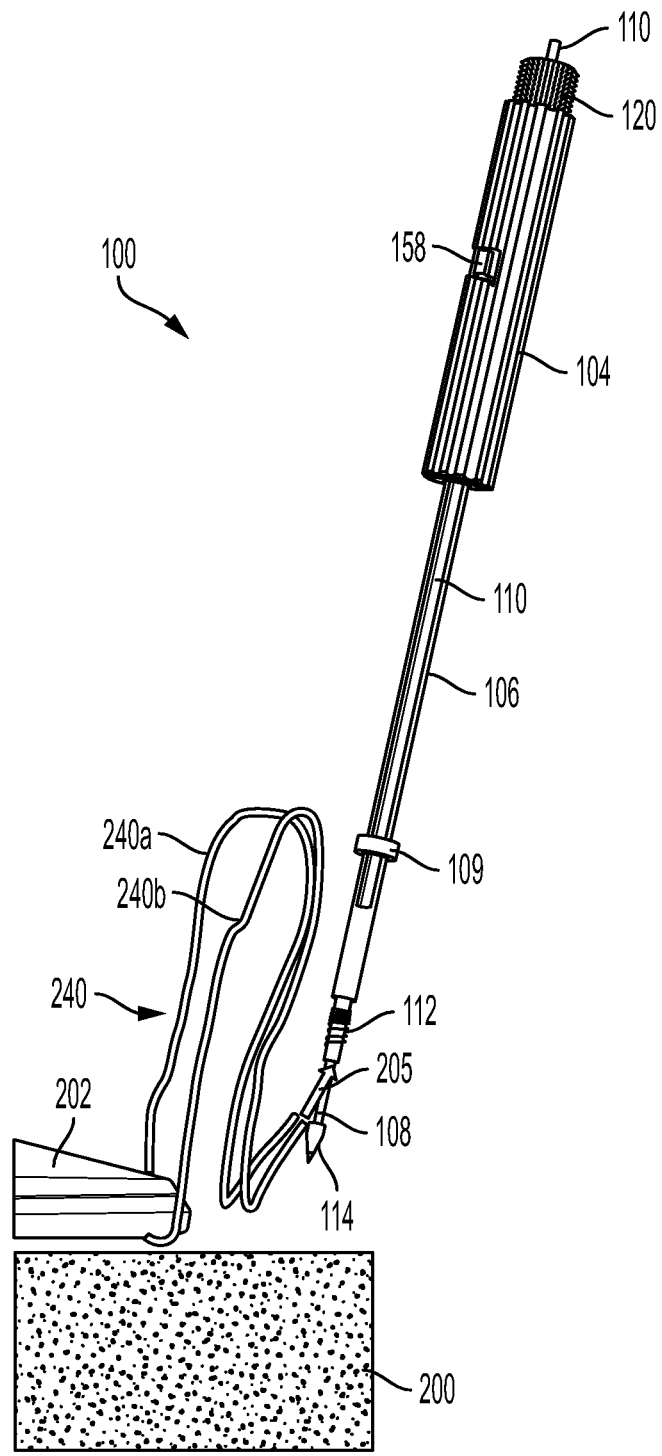
FIG. 12A is a perspective view of the surgical system of FIG. 1, showing a suture coupled thereto and the surgical system near bone.

FIG. 12A illustrates schematically (arrow 205) that terminal end portions 240a, 240b of a suture 240 (which is similar to suture 140 of FIG. 5) are coupled to the system 100 which is in the bone hole forming configuration. FIG. 12A illustrates that the suture 240 can be coupled to the tissue 202. For example, the suture 240 can be passed through or otherwise coupled to the tissue 202 such that the terminal end portions 240a, 240b of the suture 240 are free to engage with the system 100. It should be appreciated that in some embodiments the suture 240 may be pre-loaded onto the system, or the suture 240 may be passed through or otherwise coupled to the tissue 202 after being anchored in the bone using the system 100.

Figure 12B:
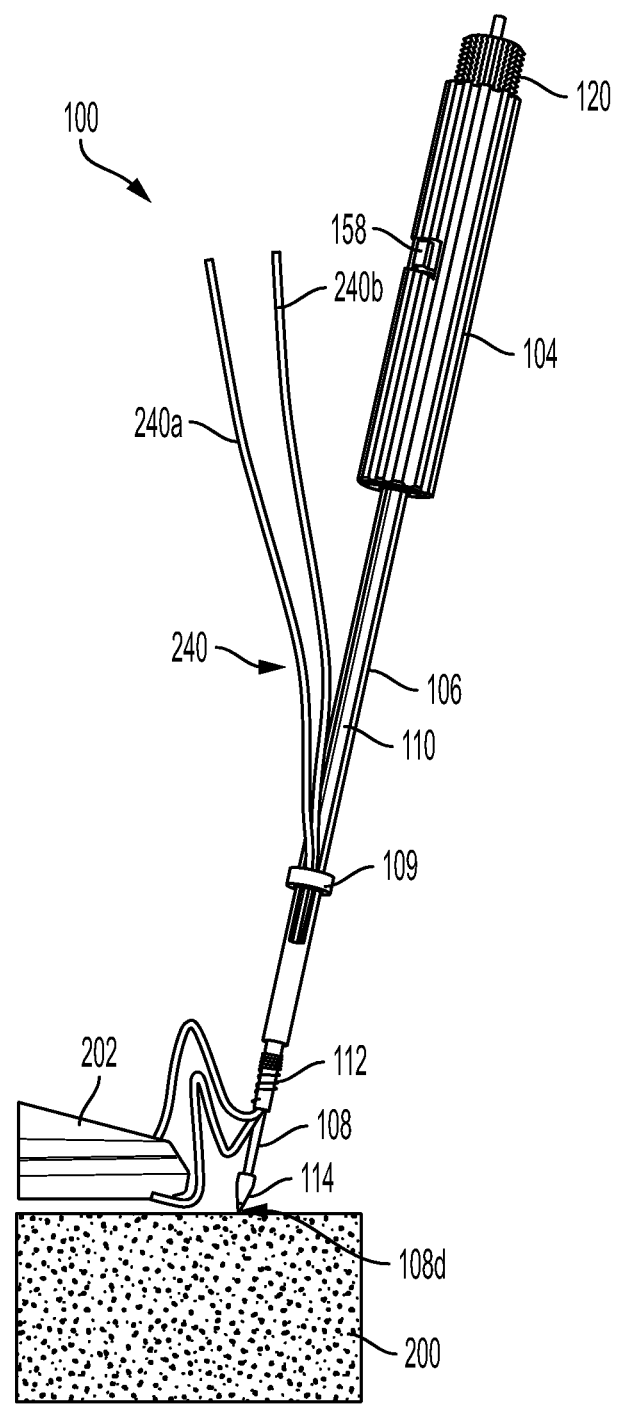
FIG. 12B illustrates the surgical system of FIG. 12A, showing a distal end of a distal awl shaft initiating a hole in the bone.

As discussed above in connection with suture 140 shown by way of example in FIG. 5, the terminal end portions 240*a*, 240*b* of the suture 240 can be passed (arrow 205) through the suture retaining feature 126 of the distal awl shaft 108 and through the lumen 113 of the suture anchor 112, and along the suture retaining feature 136 of the driver shaft 106. The terminal end portions 240*a*, 240*b* of the suture 240 are passed along a portion of the suture retaining feature 136 (e.g., slot) of the driver shaft 106 such that the terminal end portions 240*a*, 240*b* are passed under the suture holding feature 109, as shown in FIG. 12B illustrating the surgical system 100 with the suture 240 loaded thereon. In this way, the terminal end portions 240*a*, 240*b* of the suture 240 extend from the shaft 106, as also shown in FIG. 12B.

Figure 12C:
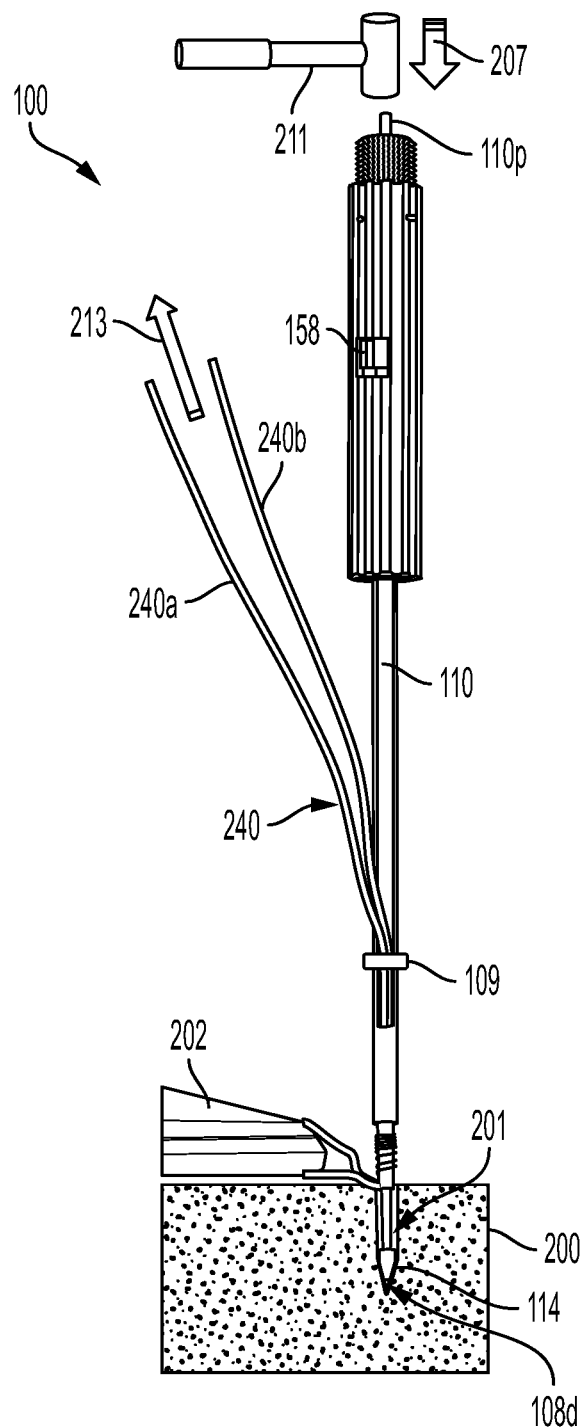
FIG. 12C illustrates the surgical system of FIG. 12B, showing the distal end of the distal awl shaft driven distally into the bone.

After the surgical system 100 with the suture 240 as shown in FIG. 12B, the distal end 108*d* of the distal awl shaft 108 is inserted into the bone 200 to initiate a hole in the bone 200 at a desired location, as shown in FIG. 12C. Tension is applied to the suture 240 after the distal end 108*d* of the distal awl shaft 108 is inserted into the bone 200 to form the hole 201. In the illustrated embodiments, the distal awl shaft 108, which has the proximal awl shaft 110 abutting thereto as discussed above, is a self-punching shaft configured to initiate and create the hole in the bone such that no additional instrument is required. Once the hole in the bone is initiated, the distal awl shaft 108 is driven further distally into the bone 200 to form a bole hole 201. In particular, as shown in FIG. 12C by arrow 207, a suitable instrument 211, such as mallet, hammer, or other instrument, is used to apply force to the proximal end 110*p* of the proximal awl shaft 110 that, in turn, applies load to the distal awl shaft 108 to thereby cause the distal awl shaft 108 to drive distally into the bone 200. As the distal awl shaft 108 is driven distally into the bone 200, the dilator feature 114 widens the hole 201. Tension can be applied to the terminal end portions 240*a*, 240*b* of the suture 240 after the distal end 108*d* of the distal awl shaft 108 is inserted into the bone 200, as shown by arrow 213 in FIG. 12C. The tensioning of the terminal suture portions 240*a*, 240*b* allows bringing the tissue 202 closer to the location of the bone hole 201, as shown schematically in FIG. 12C where the tissue 202 is disposed closer to the bone hole 201 than in FIG. 12B in which the location of the bone hole 201 to be formed is shown.

The distal end 108*d* of the distal awl shaft 108 is driven into bone 200 such that the dilator feature 114 coupled thereto is inserted into the hole 201 in the bone 200, as shown in FIG. 12C. A portion of the distal awl shaft 108 is also inserted into the hole 201, whereas the suture anchor 112 is positioned at a desired position relative to the bone hole 201. In the illustrated embodiment, as shown in FIG. 12C, before being driven into the bone, the distal end of the suture anchor 112 is positioned at the proximal edge of the bone hole 201. In other embodiments, the suture anchor 112 can be partially inserted into the bone hole.

Figure 12D:
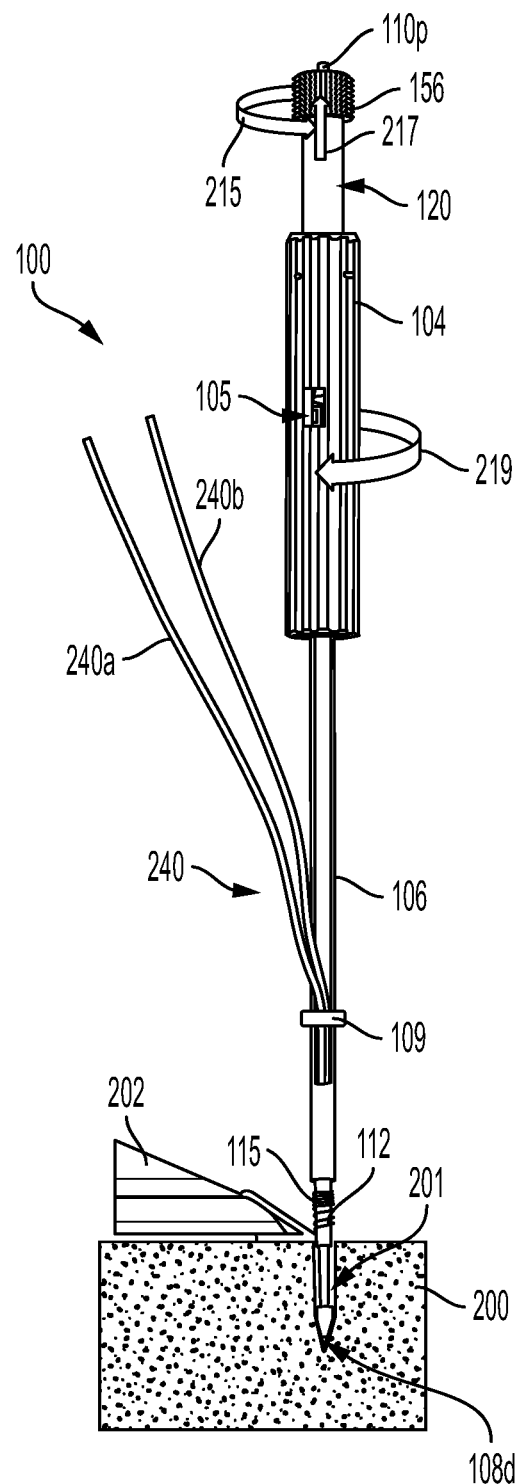
FIG. 12D illustrates the surgical system of FIG. 12C, showing a suture anchor near the bone, an awl handle activated to retract a proximal awl shaft proximally, and showing a proximal handle of a driver rotated.

Once the distal end 108*d* of the distal awl shaft 108 with the dilator feature 114 is driven into the bone 200 to a desired depth, the proximal awl shaft 110 is moved proximally away from the distal awl shaft 108. Accordingly, FIG. 12D shows that the awl handle 120 is actuated (i.e., rotated) grasping and rotating its proximal portion 156 (as shown by arrow 215) to thereby release the awl handle 120 from its engagement with the proximal handle 104 of the driver 102 as discussed above. For example, the tabs 158 of the awl handle 120, which act as stop surfaces, are disengaged from the openings 105 of the proximal handle 104, which causes the awl handle 120 to move proximally, as shown by arrow 217 in FIG. 12D. The proximal awl shaft 110 coupled to the awl handle 120 thus moves proximally to become spaced apart from the distal awl shaft 108 (as shown, for example, in FIG. 6B). Once the proximal awl shaft 110 no longer abuts the distal awl shaft 108, distal movement of the driver shaft 106 relative to the distal awl shaft 108 is no longer prevented. Also, because the proximal awl shaft 110 is moved proximally such that there is clearance between its distal end and the distal awl shaft, the proximal awl shaft 110 is thus positioned out of the way of the suture 240 so as to reduce the potential for suture entanglement during distal advancement of the driver 102.

Once the system 100 is moved from the bone hole forming configuration to the suture anchor driving configuration, the suture anchor 112 can be driven into the bone hole 201. Thus, the proximal handle 104 is rotated, as shown by arrow 219 in FIG. 12D, to cause the driver shaft 106 to rotate and to drive the suture anchor 112, coupled to the distal driver member 132 of the driver shaft 106, distally to the bone hole 201. In the illustrated embodiments, as the suture anchor 112 is advanced distally, the proximal end 108*p* of the distal awl shaft 108 does not extend proximally beyond the distal end 136*d* of the suture retaining feature 136 (e.g., slot) of the driver shaft 106.

In the illustrated embodiment, the awl handle 120 and the proximal handle 104 are shown (by arrows 215 and 219, respectively) to be rotated in opposite directions by way of example. It should be appreciated that, in other implementations, a handle coupled to a proximal awl shaft and a handle coupled to a driver shaft of a driver can be configured to be rotated in the same direction.

As the suture anchor 112 is advanced into the hole 201 in the bone 200, the threads 115 of the suture anchor 112 engage the bone 200. As the driver 102 is rotated, the distal awl shaft 108, which extends through the lumen 116 of the driver shaft 106 and through the dilator feature 114, remains stationary. The rotation of the driver 102 causes the suture anchor 112 to move distally towards the distal dilator feature 114 and into the bone 200, which causes the suture 240 to be secured between an interior wall of the bone hole 201 and an outer surface of the suture anchor 112.

Figure 12E:
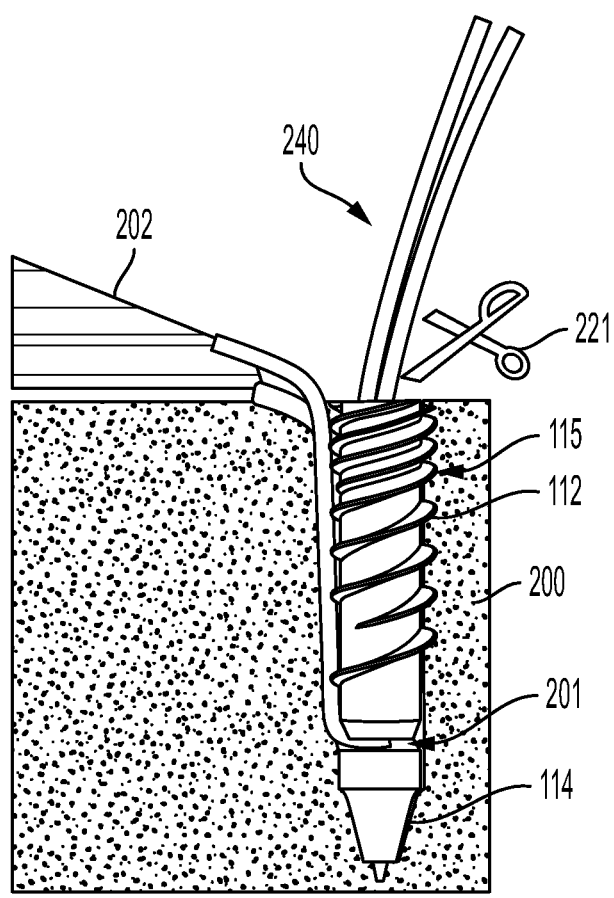
FIG. 12E illustrates the surgical system of FIG. 12D, showing the suture anchor driven into the bone and the suture secured and trimmed.

Once the suture anchor 112 has been driven into the hole 201 in the bone 200, the driver 102, as well as the distal awl shaft 108 seated therein, can be separated from the suture anchor 112. The dilator feature 114 and the suture anchor 112 with the suture 240 coupled thereto remain implanted in the bone hole 201, thereby attaching the tissue 202 to the bone 200, as shown in FIG. 12E. As shown in FIG. 12E, after the suture anchor 112 has been driven distally towards the dilator feature 114 and into the bone, the suture 240 extends proximally through at least a portion of the lumen in the suture anchor 112. If desired, the terminal end portions 240*a*, 240*b* of the suture 240 can be trimmed using a suitable cutting instrument, such as scissors 221, as shown schematically in FIG. 12E. Also, in some embodiments, the terminal end portions 240*a*, 240*b* of the suture 240 can be passed through the tissue 202, or the terminal end portions 240*a*, 240*b* can be coupled to another suture anchor, or tied to other sutures, as desired.

A system having distal and proximal awl shafts in accordance with the described techniques can have a variety of configurations. A proximal handle of the system's driver can also vary in many ways. FIGS. 13A-16B illustrate another embodiment of a system 300 which can have a distal awl shaft and a proximal awl shaft that can be moved proximally away from the distal awl shaft in an anchor insertion configuration of the system. The system 300 has a driver 302 having a proximal handle 304 and a driver shaft 306 extending distally from the handle 304. The driver 302 can have a configuration similar to that of driver 102 (FIGS. 1 and 4-11) and is therefore not described in detail. Similarly, the system 300 can have a distal awl shaft (not shown) and a proximal awl shaft 310 that are similar to distal and proximal awl shafts 108, 110 of FIGS. 2 and 3 and are therefore not described in detail. In this embodiment, an awl handle 320 coupled proximally to the proximal awl shaft 310 can have a trigger feature configured to be activated to cause the proximal awl shaft 310 to be retracted proximally away from the distal awl shaft, as discussed in more detail below. The trigger feature can be coupled to the awl handle or the trigger feature can be a separate component configured to be activated to cause the awl handle to move proximally to thereby cause the proximal awl shaft to move proximally.

Figure 16A:
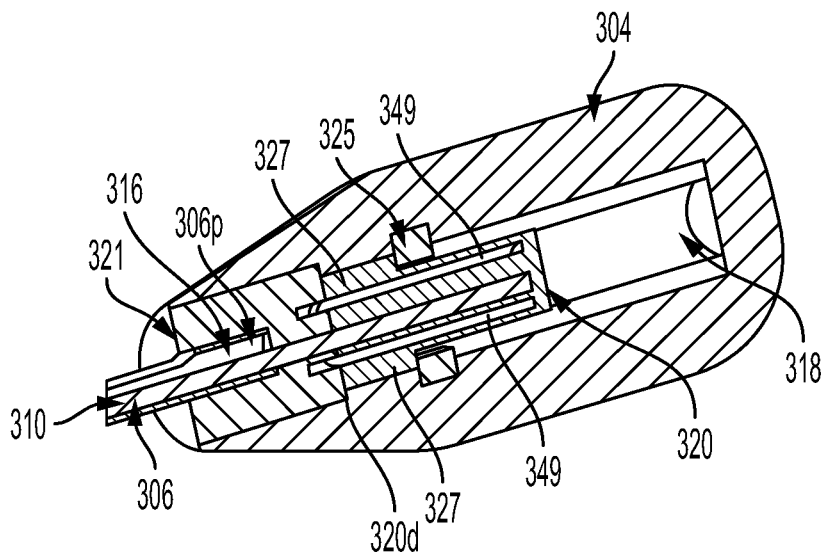
FIG. 16A is a cross-sectional view of a proximal handle of the surgical system of FIG. 13A, showing the proximal handle when the surgical system is in a bone hole forming configuration.
Figure 16B:
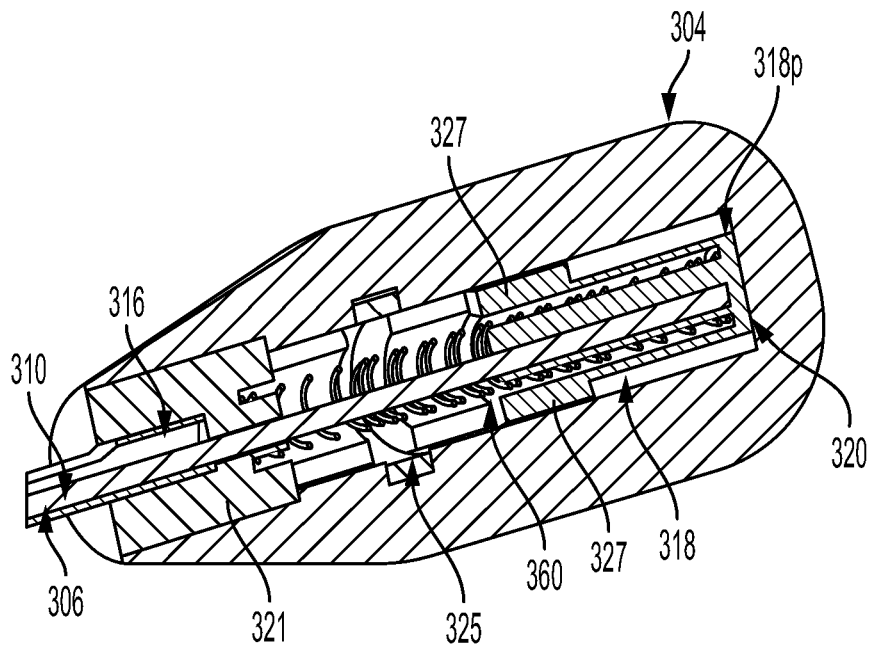
FIG. 16B is another cross-sectional view of the proximal handle of the surgical system of FIG. 13A, showing the proximal handle when the surgical system is in a suture anchor insertion configuration.

As shown in FIGS. 14, 16A, and 16B, the proximal handle 304 of the system 300 has a lumen 318 extending therethrough. As shown in FIGS. 16A and 16B, the lumen 318 has a closed end within the proximal handle 304 such that the lumen 318 has one distal opening. The lumen 318 of the proximal handle 304 is configured to receive therein the awl handle 320 having tabs 327, a spring 360, and a driver shaft holder 321.

As shown in FIG. 14, the proximal handle 304 also has a slot 323 in a side wall thereof that is configured to receive therethrough a trigger feature configured to activate the awl handle 320, such as a sliding button 325. The button 325 can be coupled to the awl handle 320 in any suitable manner. For example, the button 325 can be a separate component. The slot 323, communicating with the lumen 318 of the proximal handle 304, is configured to receive at least a portion of the sliding button 325. In this embodiment, as shown in FIG. 14, the button 325 can be a generally cylindrical member having an opening 345 therethrough. The opening 345 of the button 325 can receive a portion of the awl handle 320 therethrough, as shown in FIG. 16A discussed in more detail below. The awl handle 320 can be inserted through the opening 345 of the button 325 such that a portion of the button 325 protrudes beyond the surface of the proximal handle 304 and that portion of the button 325 can be activated (e.g., pushed towards the surface of the proximal handle 304) to thereby move the button 325 deeper into the proximal handle 304.

Figure 13A:
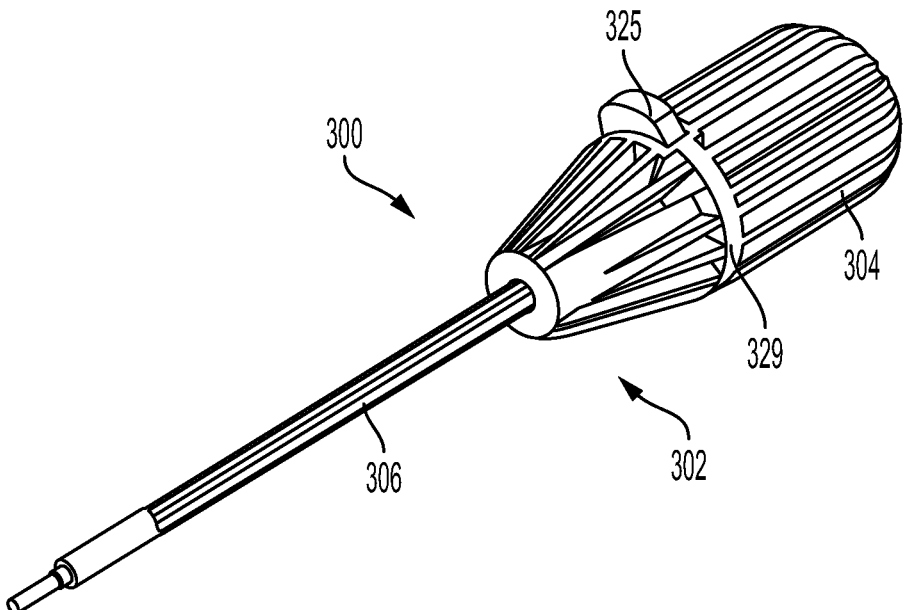
FIG. 13A is a perspective view of another embodiment of a surgical system, showing a trigger feature in a position before the trigger feature is activated.
Figure 13B:
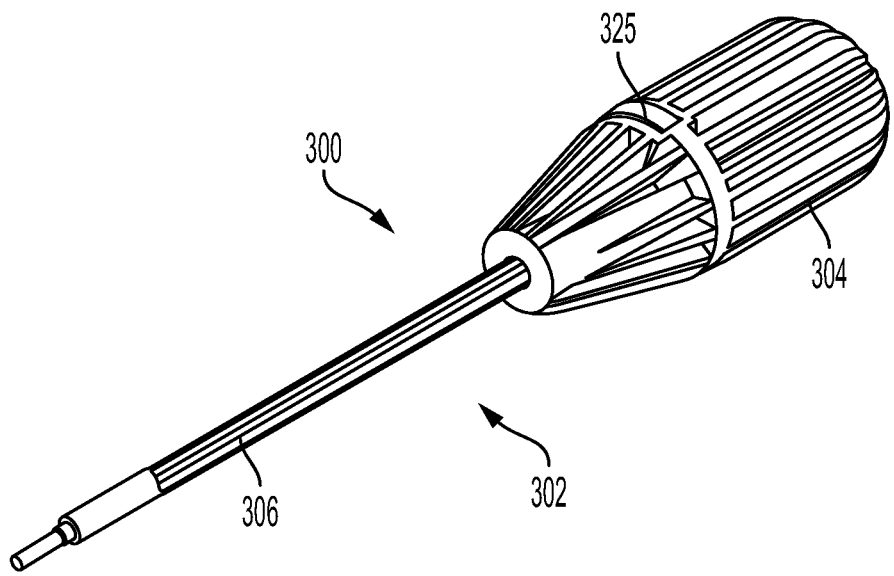
FIG. 13B is a perspective view of the surgical system of FIG. 13A, showing the trigger feature in a position after the trigger feature is activated.

As shown in FIGS. 13A, 13B, and 14, the proximal handle 304 can have a surface feature 329 disposed approximately in the middle of the handle 304. The slot 323 can be formed in relation to the feature 329 as shown in FIG. 14, and, in this example, the slot 323 is approximately centered with, and wider than feature 329.

The proximal handle 304 can have various configurations. In this embodiment, a proximal part 331p of the proximal handle 304 extending proximally from feature 329 is generally cylindrical, and a distal part 331d of the proximal handle 304 extending distally from feature 329 is generally conical (e.g., in the form of a truncated cone) and distally tapered. The proximal and distal parts 331p, 331d of the proximal handle 304 can have surface features, such as plates or ribs 333 extending along a length of the proximal and distal parts 331p, 331d, as shown in FIG. 14. The ribs 333 can have the same width, or, as in this example, some of the ribs 333, such as one or more ribs 333a extending along one or both sides of the proximal handle 304, can be wider (e.g., for reinforcement purposes). It should be appreciated that the specific shape and features of the proximal handle 304 are shown by way of example only, as the proximal handle of the driver of the system having a button-activated awl handle can have any suitable configuration, and may or may not have surface features.

The awl handle 320 can also have various configurations. In this embodiment, as shown in FIG. 14, the awl handle 320 is generally cylindrical, with the tabs 327 extending from opposed sides of an outer wall thereof. As shown in FIG. 14, the awl handle 320 has a circumferential lumen 335 formed from its distal end 320d through at least a portion of the awl handle 320. The circumferential lumen 335 is formed such that the lumen 335 is formed around a solid internal portion 337 of the awl handle 320. The circumferential lumen 335 is configured to receive a spring 360, shown in FIG. 16B (not shown in FIG. 16A, although present), and the solid internal portion 337 has a lumen 349 configured to receive therein the proximal awl shaft 310. In the illustrated embodiment, the distal end of the internal portion 337 can be in the form of a mating feature, such as a female mating feature, although other forms of a mating feature can be used.

A lumen 316 of the driver shaft 306 receives the proximal awl shaft 310 therethrough, the proximal awl shaft 310 being coupled to the awl handle 320. As shown in FIGS. 14 and 15B, the driver shaft holder 321 has a lumen 341 that is configured to receive a proximal end 306p of the driver shaft 306 such that at least a portion of the driver shaft 306 is coupled thereto. The lumen 341 extends between a distal-facing surface 321d and the proximal-facing surface 321p of the driver shaft holder 321. As shown in FIGS. 14 and 15A, the driver shaft holder 321 is configured to mate with a corresponding female mating feature at the distal end of the lumen 318 of the handle 304.

The system 300 can be used in a surgical procedure similar to the way in which system 100 is used, as shown in FIGS. 12A to 12E. In a bone hole forming configuration of the system 300, the sliding button 325 is configured to protrude beyond the outer wall of the proximal handle 304, as shown in FIG. 13A. In such a configuration, as shown in FIG. 16A, the tabs 327 of the awl handle 320 abut the sliding button 325 distally such that the awl handle 320 is prevented from being moved proximally. The spring 360 (not shown in FIG. 16A) can be disposed within the circumferential lumen 335 of the awl handle 320 in at least partially compressed configuration.

To move the system 300 from the bone hole forming configuration to a suture anchor insertion configuration, the button 325 can be activated, such as pressed or pushed towards the outer surface of the proximal handle 304, as shown in FIG. 13B. This causes the button 325 to be moved deeper into the slot 323 of the proximal handle 304 and thereby release the tabs 327 of the awl handle 320 from engagement with the button 325. FIG. 13B shows that, for activation, the button 325 can be pushed until it is disposed substantially flush with the surface of the proximal handle 304. However, in other implementations, the button 325 can be otherwise disposed after its activation.

Figure 16C:
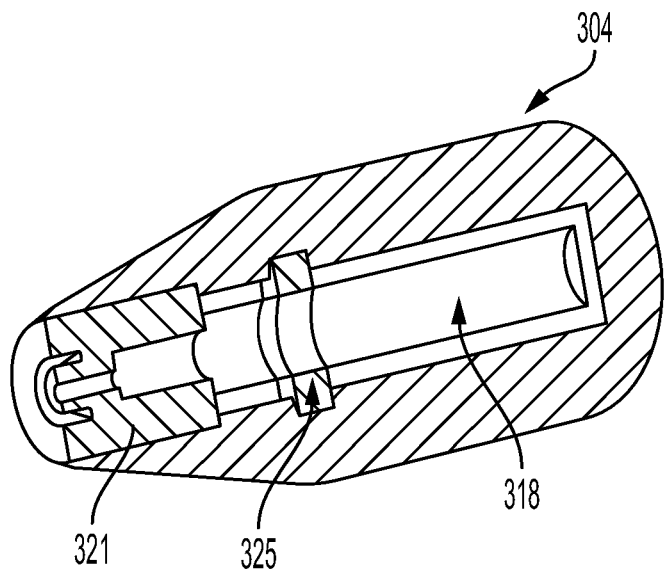
FIG. 16C is a cross-sectional, partial view of the proximal handle of FIG. 16A.
Figure 16D:
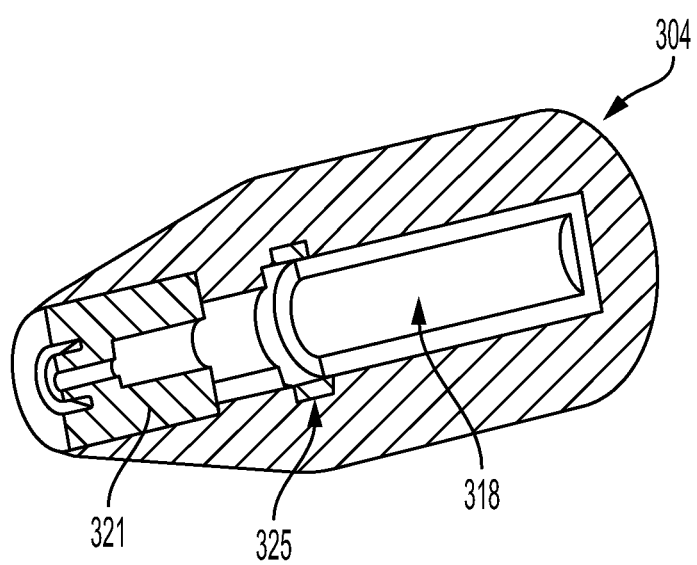
FIG. 16D is a cross-sectional, partial view of the proximal handle of FIG. 16B.

FIGS. 16C and 16D additionally illustrate the button 325 of the proximal handle 304, while not all components are shown for ease of illustration purposes only. Thus, FIG. 16C shows the proximal handle 304 having the button 325 in the bone hole forming configuration of the system 300, i.e. the button 325 is not activated, and the tabs 327 of the awl handle 320 are engaged with the button. FIG. 16D shows the proximal handle 304 with the button 325 in the suture anchor insertion configuration of the system, i.e. the button 325 is activated, such as depressed, and the tabs 327 of the awl handle 320 have been released from engagement with the button 325.

As shown in FIG. 16B, the activation of the button 325 allows the awl handle 320 to move proximally within the proximal handle's lumen 318, thus the proximal awl shaft 310, coupled to the awl handle 320, is also caused to move proximally. The spring 360 within the circumferential lumen 335 of the awl handle 320 can move from the least partially compressed configuration to a less compressed configuration and thereby biases the awl handle 320 proximally and maintains the awl handle 320 in such position. In this way, the proximal awl shaft 310 is spaced proximally apart from the distal awl shaft and the system's driver 302 can be used (e.g., by rotating the proximal handle 304) to drive a suture anchor (not shown) into a bone hole. In this example, the awl handle 320 is moved proximally so as to abut a proximal end 318p of the proximal handle's lumen 318. Thus, the lumen 318 of the proximal handle 304 can be configured such that the awl handle 320 is moved to a predetermined distance to thereby move the proximal awl shaft 310 proximally to that distance.

A surgical system can have any other configurations of a proximal handle and an awl handle. Also, the awl handle can have various trigger features configured to be activated to cause a proximal awl shaft coupled to the awl handle to move proximally. Also, the trigger feature can be configured such that the proximal awl shaft is retracted proximally, away from a distal awl shaft, without being rotated.

Figure 17:
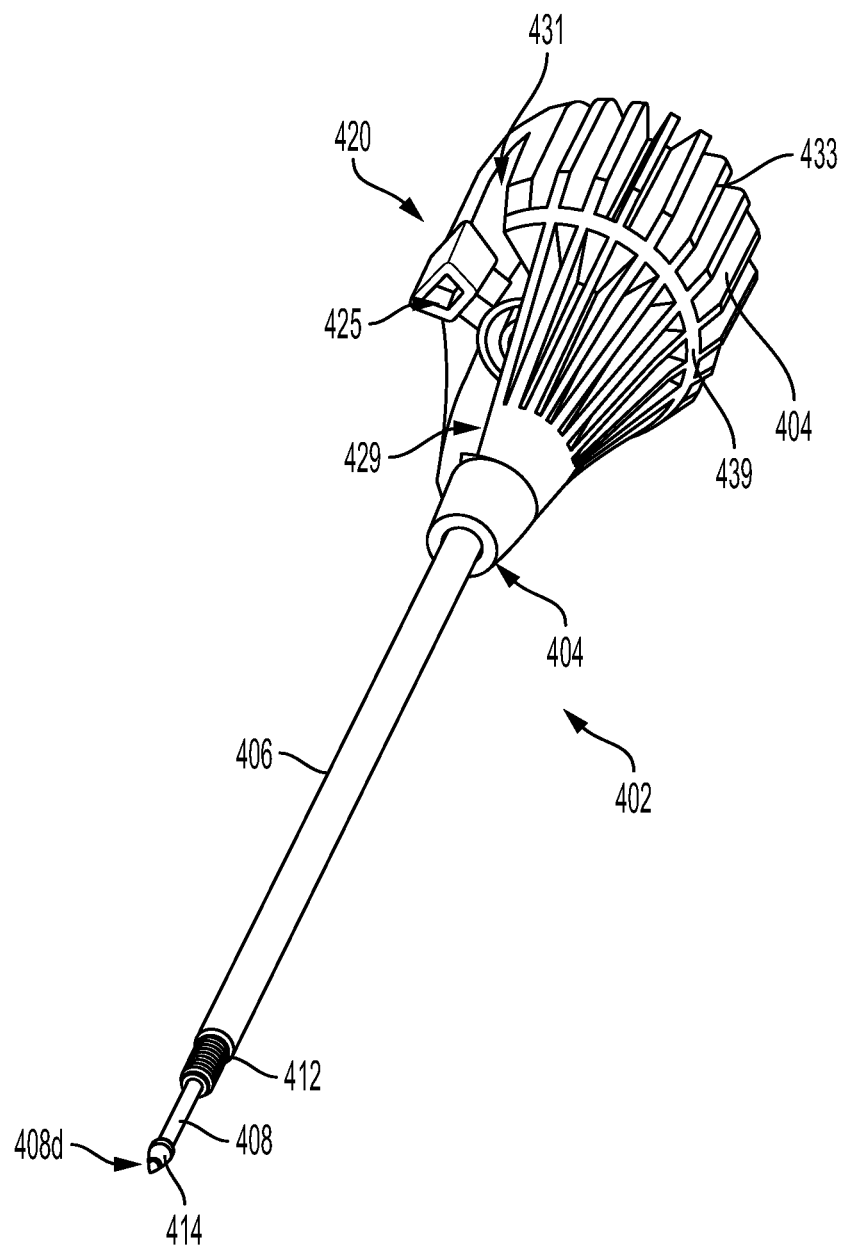
FIG. 17 is a perspective view of another embodiment of a surgical system, showing a trigger feature of an awl handle in a position before the trigger feature is activated.

FIGS. 17-21B illustrate another embodiment of a surgical system 400 having a driver device or driver 402 that includes a proximal handle 404 and a driver shaft 406. Similar to system 100 (FIG. 1), the system 400 includes a suture anchor 412 coupled to a distal driver member of the driver shaft 406, a proximal awl shaft (not shown) having an awl handle 420 coupled proximally thereto, and a distal awl shaft 408 extending at least partially through the driver shaft 406. As shown in FIG. 17, also similar to system 100, the system 400 can include a dilator feature 414 which is distal to the suture anchor 412 and has a distal portion of the distal awl shaft 408 at least partially extending therethrough such that at least a portion of a distal tip 408d of the distal awl 408 shaft extends distally from a distal end of the dilator feature 414. The dilator feature 414 can be implantable.

Figure 18:
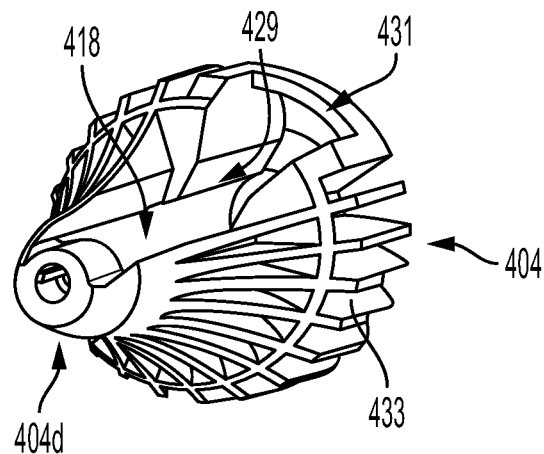
FIG. 18 is a perspective view of a proximal handle of the surgical system of FIG. 17.
Figure 19:
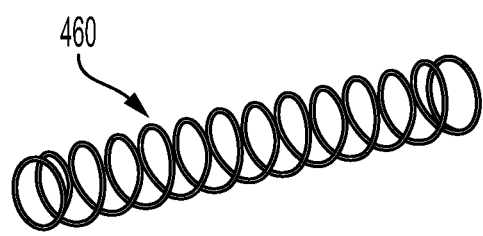
FIG. 19 is a perspective view of a spring disposed in the proximal handle of the surgical system of FIG. 17.
Figure 20:
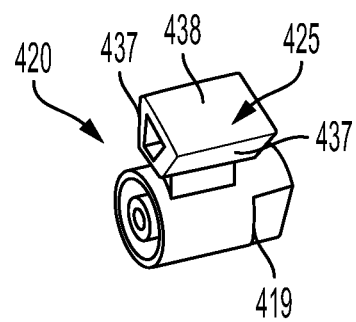
FIG. 20 is a perspective view of an awl handle of the surgical system of FIG. 17.

The proximal handle 404 can receive in a lumen 418 thereof the awl handle 420 that includes a generally cylindrical body 419 and a button or knob 425 that extends from the outer surface of the body 419, as shown in FIGS. 17, 18, and 20. The lumen 418 of the proximal handle 404 communicates with a slot 429 formed in the outer wall of the proximal handle 404 along a portion of the length of the handle 404. In this way, the awl handle 420 is movably (e.g., slidably) seated within the lumen 418 and the slot 429 such that the knob 425 thereof protrudes at least partially beyond the outer surface of the proximal handle 404, as shown in FIG. 17. The knob 425 is configured to be activated to move the awl handle 420 along the slot 429. The distal end 404d of the proximal handle 404 receives therein a proximal portion of the driver shaft 106.

The inner walls of the slot 429 and at least a portion of the lumen 418 of the proximal handle 404 can be configured to conform at least partially to the configuration of the awl handle 420. For example, at least a portion of the lumen 418 is generally cylindrical to movably seat therein the body 419 of the awl handle 420. Further, in the illustrated example, the inner side walls of the slot 429 can be configured to seat the knob 425 of the awl handle 420 that has corresponding surfaces 437 at opposed sides thereof. As shown in FIG. 20, the knob 425 has a top surface 438 that can be substantially flat and that has the surfaces 427 on opposed sides thereof that are slanted towards each other and sit on top of the body 419 of the awl handle 420. In this example, a bore in the knob 425 can be formed between the slanted surfaces 427, though it should be appreciated that the knob 425 can have any other configurations. It should be appreciated that the awl handle 420, including the knob 425 thereof, are shown by way of example only, and that the awl handle can have any suitable configurations and can have other trigger features configured to be grasped or otherwise activated to move the awl handle.

Figure 21A:
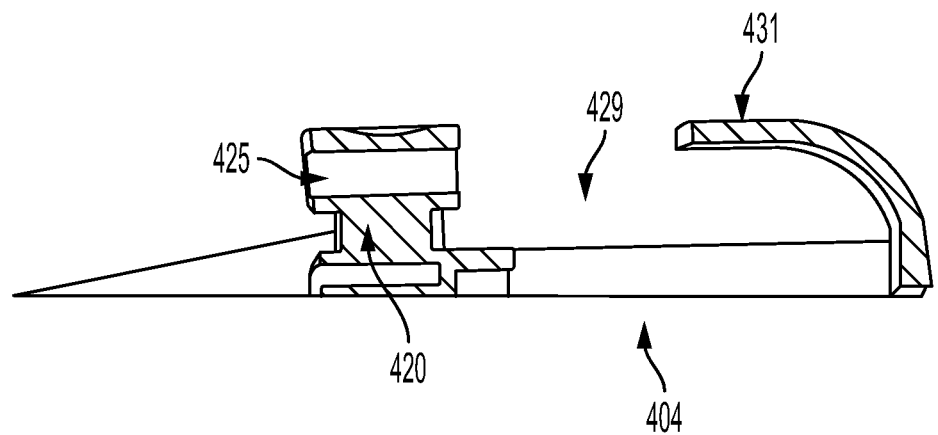
FIG. 21A is a side cross-sectional view of a proximal handle of the surgical system of FIG. 17, showing the trigger feature of the awl handle in a position before the trigger feature is activated.

The system 400 can be used in a surgical procedure similar to the way in which system 100 is used, as shown in FIGS.-12E. In a bone hole forming configuration of the system 400, the awl handle 420 is seated in the lumen 418 of the proximal handle 404 and in the slot 429 such that the knob 425 protrudes beyond the outer surface of the proximal handle 404, as shown in FIG. 21A. In such a configuration, as in other embodiments described herein, a distal end of the proximal awl shaft abuts a proximal end of the distal awl shaft 408.

Figure 21B:
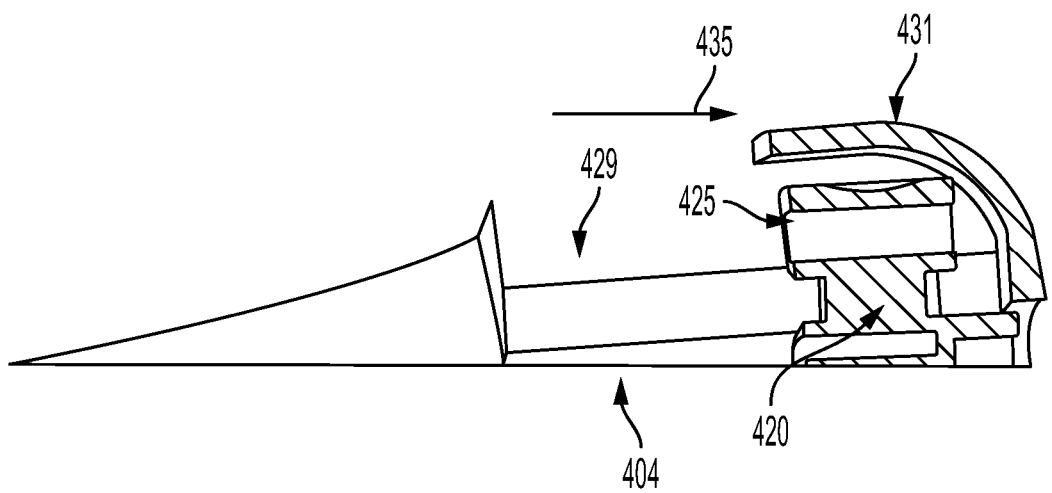
FIG. 21B is another side cross-sectional view of the proximal handle of the surgical system of FIG. 17, showing the trigger feature of the awl handle activated to thereby move the awl handle and a proximal awl shaft coupled thereto proximally.

Once the bone hole has been formed, to move the system 400 from the bone hole forming configuration to a suture anchor insertion configuration, the handle 420 can be activated—(e.g., pushing on the knob 425 to move the handle 420 toward the central axis of the driver), resulting in motion of the knob (and the attached proximal awl shaft) proximally relative to the rest of the driver 402 (as shown schematically by arrow 435 in FIG. 21B). In this way, the awl handle 420 moves proximally so as to abut distally the inner surface of a portion 431 of the proximal handle 404, as shown in FIG. 21B. The portion 431 can have any suitable configuration. A spring 460 (FIG. 19), which can be disposed in the lumen 418 of the proximal handle 404, can move from at least partially compressed to a less compressed configuration to thereby bias the awl handle 420 proximally. Similar to spring 360 of system 300 shown in FIGS. 14 and 16B, the spring 460 can be disposed, for example, in a circumferential lumen of the awl handle 420. However, the spring 460 can otherwise be associated with the awl handle 420. The proximal movement of the awl handle 420 causes the proximal awl shaft coupled thereto to also move proximally and thus become spaced apart from the distal awl shaft 408. In this configuration, the driver 402 of the system 400 can be used (e.g., by rotating the proximal handle 404) to drive the suture anchor 412 into the bone hole.

It should be appreciated that the proximal handle 404 can have various surface features. For example, similar to the proximal handle 304 (FIGS. 13A, 13B, and 14), the proximal handle 404 can have ribs. For example, in the illustrated embodiment, the proximal handle 404 can have ribs 433 formed along at least a portion of a length thereof. As shown in FIGS. 17 and 18, a portion of the proximal handle 404 adjacent to the distal end 404d of the handle 404 is free of the ribs. Also, similar to proximal handle 304, the proximal handle 404 of FIG. 17 can include a feature 439 formed on the outer wall thereof around at least a portion of its circumference. The Feature 439 can be disposed between a substantially cylindrical proximal portion of the proximal handle 404 and a distally tapered distal portion of the proximal handle 404. However, again, the proximal handle 404 can have any other suitable shapes, configurations, and features that facilitate grip and operation of the proximal handle 404.

The methods and systems described herein can have different variations. For example, in each of the embodiments, multiple sutures can be used to couple tissue to bone. Also, one or more sutures can be loaded on a surgical system before or during a surgical procedure. For example, in some embodiments, a surgical system can have at least one suture pre-loaded thereto such that the surgical system in the assembled configuration includes the suture. Furthermore, in some embodiments, the dilator feature may not be used. As another variation, another feature can be used to dilate a hole in bone.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device, e.g., the shafts, can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the components of the system described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred the components are sterilized. This can be done by any number of ways known to those skilled in the art including beta or gamma radiation, ethylene oxide, steam, and a liquid bath (e.g., cold soak).

One skilled in the art will appreciate further features and advantages of the described subject matter based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical system, comprising:
 a first elongate shaft;
 a second elongate shaft that is axially aligned with the first elongate shaft and is located distal to the first elongate shaft;
 a suture anchor operably coupled to the second elongate shaft; and
 an actuator configured to be actuated to move the surgical system from a first configuration to a second configuration;
 wherein, in the first configuration, the surgical system is configured to initiate a hole in bone with the first elongate shaft applying a load to the second elongate shaft, and the suture anchor is prevented from being moved distally relative to the second elongate shaft; and
 in the second configuration, the suture anchor is configured to move distally relative to the second elongate shaft to be driven into the bone.

2. The system of claim 1, wherein the first and second elongate shafts are separate elements;
 in the first configuration, a distal end of the first elongate shaft abuts a proximal end of the second elongate shaft; and
 in the second configuration, the distal end of the first elongate shaft is spaced a distance proximal to the proximal end of the second elongate shaft.

3. The system of claim 1, wherein the first elongate shaft is biased in a proximal direction; and
 the actuation of the actuator is configured to reduce the bias such that the first elongate shaft automatically moves proximally relative to the second elongate shaft.

4. The system of claim 1, wherein, in the first configuration, one or more tabs operably coupled to the first elongate shaft engage the actuator; and
 the actuation of the actuator is configured to cause the one or more tabs to move and thereby no longer engage the actuator.

5. The system of claim 1, wherein the actuation of the actuator includes rotating the actuator about a longitudinal axis of the first elongate shaft.

6. The system of claim 1, wherein the actuator includes a trigger; and
 the actuation of the actuator includes pressing the trigger.

7. The system of claim 1, further comprising a driver;
 wherein the suture anchor is mounted on the driver; and
 with the surgical system in the second configuration, the driver is configured to drive the suture anchor over the second elongate shaft and into the bone.

8. The system of claim 7, wherein, in the first configuration, the driver is prevented from moving distally relative to the second elongate shaft; and
 with the surgical system in the second configuration, the driver is not prevented from moving distally relative to the second elongate shaft.

9. The system of claim 7, wherein the driver includes a lumen having the first and second elongate shafts located therein; and
 with the surgical system in the first configuration, the first elongate shaft extends distally beyond the driver.

10. The system of claim 1, wherein a distal tip of the second elongate shaft is configured to penetrate into the bone to initiate the hole in the bone; and
 the surgical system further comprises a dilator located proximal to the distal tip of the second elongate shaft and distal to the suture anchor, the dilator being configured to widen the hole initiated by the distal tip of the second elongate shaft.

11. The system of claim 10, wherein the dilator is configured to be implantable in a body of a patient; and
 the dilator is configured to be implanted in the bone distal to the suture anchor.

* * * * *